US007090991B2

(12) United States Patent
Oehlen

(10) Patent No.: US 7,090,991 B2
(45) Date of Patent: Aug. 15, 2006

(54) SYSTEM FOR DETECTION OF A FUNCTIONAL INTERACTION BETWEEN A COMPOUND AND A CELLULAR SIGNAL TRANSDUCTION COMPONENT

(75) Inventor: Lambertus J. Oehlen, Tarrytown, NY (US)

(73) Assignee: Cadus Technologies, Inc., New York, NY (US)

( * ) Notice: Subject to any disclaimer, the term of this patent is extended or adjusted under 35 U.S.C. 154(b) by 76 days.

(21) Appl. No.: 10/404,018

(22) Filed: Mar. 31, 2003

(65) Prior Publication Data

US 2003/0211615 A1    Nov. 13, 2003

Related U.S. Application Data

(62) Division of application No. 09/592,010, filed on Jun. 12, 2000, now Pat. No. 6,555,325.

(60) Provisional application No. 60/139,021, filed on Jun. 14, 1999.

(51) Int. Cl.
*G01N 33/53* (2006.01)
*C12Q 1/68* (2006.01)
(52) U.S. Cl. .......................... 435/7.31; 435/6; 435/7.2
(58) Field of Classification Search .................... 435/4, 435/6, 7.1, 7.2, 7.31
See application file for complete search history.

(56) References Cited

U.S. PATENT DOCUMENTS

| | | | | |
|---|---|---|---|---|
| 4,418,149 | A | 11/1983 | Ptashne et al. | 435/253 |
| 4,833,080 | A | 5/1989 | Brent et al. | 435/172.3 |
| 4,948,874 | A | 8/1990 | Kronvall et al. | 350/350 |
| 5,096,815 | A | 3/1992 | Ladner et al. | 435/69.1 |
| 5,283,173 | A | 2/1994 | Fields et al. | 435/6 |
| 5,401,629 | A | 3/1995 | Harpold et al. | 435/6 |
| 5,436,128 | A | 7/1995 | Harpold et al. | 435/6 |
| 5,468,614 | A | 11/1995 | Fields et al. | 435/6 |
| 5,482,835 | A | 1/1996 | King et al. | 435/6 |
| 5,576,210 | A * | 11/1996 | Sledziewski et al. | 435/254.21 |
| 5,580,736 | A | 12/1996 | Brent et al. | 435/6 |
| 5,691,188 | A | 11/1997 | Pausch et al. | 435/225.1 |
| 5,703,220 | A | 12/1997 | Yamada et al. | 536/23.5 |
| 5,739,029 | A | 4/1998 | King et al. | 435/254.21 |
| 5,789,184 | A | 8/1998 | Fowlkes et al. | 435/7.31 |
| 5,846,819 | A | 12/1998 | Pausch et al. | 435/320.1 |
| 5,876,951 | A | 3/1999 | Fowlkes et al. | 435/7.31 |
| 5,879,591 | A | 3/1999 | Nagoh et al. | 252/586 |
| 6,100,042 | A | 8/2000 | Fowlkes et al. | 435/7.1 |
| 6,251,605 | B1 * | 6/2001 | Ostanin et al. | 435/6 |

FOREIGN PATENT DOCUMENTS

| | | |
|---|---|---|
| EP | 568925 | 11/1993 |
| WO | WO 88/10308 | 12/1988 |
| WO | WO 91/12273 | 8/1991 |
| WO | WO 92/05244 | 4/1992 |
| WO | WO 92/08740 | 5/1992 |
| WO | WO 93/10230 | 5/1993 |
| WO | WO 94/23025 | 10/1994 |
| WO | WO 95/30012 | 11/1995 |
| WO | WO 97/11159 | 3/1997 |
| WO | WO 98/13513 | 4/1998 |
| WO | WO 99/18211 | 4/1999 |

OTHER PUBLICATIONS

Achstetter, T. "Regulation of alpha-factor production in *Saccharomyces cerevisiae*: a-factor pheromone-inducced expression of the MF alpha 1 and STE13 genes," *Mol. Cell. Biol.* 9(10):4507-14 (1989).
Akada, R. et al. "Genetic Relationships Between the G Protein βγ Complex, Ste5p, Ste20p and Cdc42p: Investigation of Effector Roles in the Yeast Pheromone Response Pathway," *Genetics* 143:103-117 (1996).
Alison, Malcolm R. et al. "Growth factors and growth factor receptors," *Brit. J. of Hosp. Med.* 49(11):774-88 (1993).
Altieri, Dario C. "Proteases and protease receptors in modulation of leukocyte effector functions," *J. of Leukocyte Biol.* 58:120-27 (1995).
Artemyev, Nikolai O. et al. "Sites of Interaction between Rod G-Protein α-Subunit and cGMP-phosphodiesterase γ-Subunit," *J. Biol. Chem.* 267(35):25067-72 (1992).
Banuett, "Signalling in the yeasts: an informational cascade with links to the filamentous fungi," *Microbiol. Mol. Biol. Rev.* 62(2):249-74 (1998).
Belka, C. et al. "The role of tyrosine kinases and their substrates in signal transmission of hematopoietic growth factors: a short review," *Leukemia* 9:754-61 (1995).

(Continued)

*Primary Examiner*—Ruixiang Li
(74) *Attorney, Agent, or Firm*—Edwards Angell Palmer & Dodge, LLP; Peter C. Lauro, Esq.

(57) ABSTRACT

The present invention makes available a rapid, reproducible, robust assay system for screening and identifying pharmaceutically effective compounds that specifically interact with and modulate the activity of a cellular protein, e.g., a receptor. or ion channel. The subject assay enables rapid screening of large numbers of compounds to identify those which act as an agonist or antagonist to the bioactivity of the cellular protein. In this system, the first cell is treated with a compound, and functional interaction of this compound with a cellular receptor yields a secreted signal. A second cell, bearing a receptor for this secreted signal, makes use of an indicator gene in a signaling pathway coupled to this second receptor. The subject assays include methods of identifying compounds which specifically modulate, for example, heterologous receptors coupled to the pheromone response pathway in yeast. The subject assays are particularly amenable to the identification of specific agonists and antagonists of G protein-coupled receptors.

23 Claims, 2 Drawing Sheets

OTHER PUBLICATIONS

Bender, Alan and Sprague, George F. Jr. "Pheromones and Pheromone Receptors Are the Primary Determinants of Mating Specificity in the Yeast *Saccharomyces cerevisiae*," *Genetics* 121:463-76 (1989).

Birnbaumer, Lutz "Transduction of receptor signal into modulation of effector activity by G proteins: the first 20 years or so . . . " *FASEB Journal* 4:3178-88 (1990).

Blinder, Dmitry et al. "Constitutive Mutants in the Yeast Pheromone Response: Ordered function of the Gene Products," *Cell* 56:479-486 (1989).

Brill, Julie A. et al. "A Role for Autophosphorylation Revealed by Activated Alleles of FUS3, the Yeast MAP Kinase Homolog," *Molecular Biology of the Cell* 5:297-312 (1994).

Burack, W. Richard et al. "The Activating Dual Phosphorylation of MAPK by MEK Is Nonprocessive," *Biochemistry* 36(20):5929-5933 (1997).

Cartwright, C.P. et al., "In vivo topological analysis of Ste2, a yeast plasma membrane protein, by using beta-lactamase gene fusions," *Mol Cell Biol.* 11(5):2620-8 (1991).

Cavallini, Bruno et al. "A yeast activity can substitute for the HeLa Cell TATA box factor," *Nature* 334:77-80 (1988).

Chambers, D. A. et al. "Neuroimmune Modulation: Signal Tranduction and Catecholamines," *Neurochem. Int.* 22(2):95-110 (1993).

Chan, Russell K. and Otte, Carol A. "Isolation and Genetic Analysis of *Saccharomyces cerevisiae* Mutants Supersensitive to G1 Arrest by a Factor and α Factor," *Molecular and Cellular Biol.* 2(1):11-20 (1982).

Chang, Fred and Herskowitz, Ira "Identification of a Gene Necessary for Cell Cycle Arrest by a Negative Growth Factor of Yeast: FAR1 is an Inhibitor of a G1 Cyclin, CLN2," *Cell* 63:999-1011 (1990).

Chen, R. et al., "Expression cloning of a human corticotropin-releasing-factor receptor," *Proc Natl Acad Sci U S A.* 90(19):8967-71 (1993).

Chien, Cheng-Ting, et al. "The two-hybrid system: A method to identify and clone genes for proteins that interact with a protein of interest," *Proc. Natl. Acad. Sci. USA* 88:9578-82 (1991).

Clark, Karen L. et al. "Interactions among the Subunits of the G-protein Involved in *Saccharomyces cerevisiae* Mating," *Molecular and Cellular Biol.* 13(1):1-8 (1993).

Cole, Gary M. et al. "Stoichiometry of G Protein Subunits Affects the *Saccharomyces cerevisiae* Mating Pheromone Signal Transduction Pathway," *Molecular and Cellular Biology* 10(2):510-517 (1990).

Coleman, David E. et al. "Structures of Active Conformation of $G_{i\alpha 1}$ and the Mechanism of GTP Hydrolysis," *Science* 265:1405-12 (1994).

Conklin, Bruce R. et al. "Substitution of three amino acids switches receptor specificity of $G_{q\alpha}$ to that of $G_{i\alpha}$," *Nature* 363:274-76 (1993).

Corness, J.D. et al., "A human somatostatin receptor (SSTR3), located on chromosome 22, displays preferential affinity for somatostatin-14 like peptides," *FEBS Lett.* 321(2-3):279-84 (1993).

Cwirla, Steven E. et al. "Peptides on phage: A vast library of peptides for identifying ligands," *Proc. Natl. Acad. Sci. USA* 87:6378-82 (1990).

Devlin, James J. et al. "Random Peptide Libraries: A Source of Specific Protein Binding Molecules," *Science* 249:404-6 (1990).

Dietzel, Christine and Kurjan, Janet "The Yeast SCG1 Gene: A Gα-like Protein Implicated in the a- and α-Factor Response Pathway," *Cell* 50:1001-10 (1987).

Dmochowska, Aleksandra et al. "Yeast *KEX1* Gene Encodes a Putative Protease with a Carboxypeptidase B-like Function Involved in Killer Toxin and α-Factor Precursor Processing," *Cell* 50:573-84 (1987).

Dolan, J. W. et al. "Overproduction of the yeast STE12 protein leads to constitutive transcriptional induction," *Genes & Development* 4(4):492-502 (1990).

Dubois, Patrice M. et al. "Role of the transmembrane and cytoplasmic domains of surface IgM in endocytosis and signal transduction," *Eur. J. Immunol.* 22:851-57 (1992).

Erickson, Deborah "Intercepted Messages: New biotechnology drugs target intracellular communication," *Scientific American* 267(5):122-23 (1992).

Etienne, Gilles et al. "A Screening Method for Antifungal Substances Using *Saccharomyces cerevisiae* Strains Resistant to Polyene Macrolides," *J. of Antibiotics* 43(2):199-206 (1990).

Fasullo, Michael T. and Davis, Ronald W. "Direction of Chromosome Rearrangements in *Saccharomyces cerevisiae* by Use of *his3* Recombination Substrates," *Molecular and Cellular Biol.* 8(10):4370-80 (1988).

Ferrell, James E. Jr. et al. "The Biochemical Basis of an All-or-None Cell Fate Switch in *Xenopus* Oocytes," *Science* 280:895-898 (1998).

Ferrell, James E. Jr. "Tripping the switch fantastic: how a protein kinase cascade can convert graded inputs into switch-like outputs," *Trends In Biochem. Sci.* 21(12);460-6 (1996).

Fields, Stanley and Song Ok-kyu "A novel genetic system to detect protein-protein interactions," *Nature* 340:245-46 (1989).

Franke, Arthur E. et al. "Human C5a Anaphylatoxin: Gene Synthesis, Expression, and Recovery of Biologically Active Material from *Escherichia coli*," *Methods in Enzymology* 162:653-68 (1988).

Funaro, Ana et al. "Human CD38 is associated to distinct molecules which mediate transmembrane signaling in different lineages," *Eur. J. Immunol.* 23:2407-11 (1993).

Gallego, Carme et al. "Myristoylation of the $G_{\alpha i2}$ polypeptide, a G protein α subunit, is required for its signaling and transformation functions," *Proc. Natl. Acad. Sci. USA* 89:9695-99 (1992).

Garritsen, Anja et al. "The N-Terminal coiled-coil domain of β is essential for γ association: A Model for G-Protein βγ subunit interaction," *Proc. Natl. Acad. Sci. USA* 90:7706-10 (1993).

Gerard, Norma P. and Gerard, Craig "Construction and Expression of a Novel Recombinant Anaphylatoxin, C5a-N19, a Probe for the Human C5a Receptor," *Biochemistry* 29(39):9274-81 (1990).

Gordon, J. "B-cell signaling via the C-type lectins CD23 and CD72," *Immunology Today* 15(9):411-17 (1994).

Graf, Rolf et al. "A Truncated Recombinant α Subunit of $G_{i3}$ with a Reduced Affinity for βγ Dimers and Altered Guanosine 5'-3-O-(Thio)triphosphate Binding," *J. of Biol. Chem.* 267(34):24307-14 (1992).

Gros, Philippe et al. "Mammalian Multidrug Resistence Gene: Complete cDNA Sequence Indicates Strong Homology to Bacterial Transport Proteins," *Cell* 47:371-80 (1986).

Guthrie et al., in *Guide to Yeast Genetics and Molecular Biology*, Guthriee, Fink (Eds.), 194:77-93 (1991).

Gyuris, Jenö et al. "Cdi1, A Human G1 and S Phase Protein Phosphatase That Associates with Cdk2," *Cell* 75:791-803 (1993).

Hagen, David C. et al. "Evidence the yeast *STE3* gene encodes a receptor for the peptide pheromone a factor: Gene sequence and implications for the structure of the presumed receptor," *Proc. Natl. Acad. Sci. USA* 83:1418-22 (1986).

Harbury, Pehr B. et al. "A Switch Between Two-, Three- and Four-Stranded Coiled Coils in GCN4 Leucine Zipper Mutants," *Science* 262:1401-07 (1993).

Hartwell, Leland H. "Mutants of *Saccharomyces cerevisiae* Unresponsive to Cell Division Control by Polypeptide Mating Hormone," *J. Cell Biol.* 85:811-22 (1980).

Hasson, M.S. et al. "Mutational Activation of the *STE5* Gene Product Bypasses the Requirement for G Protein β and γ Subunits in the Yeast Pheromone Response Pathway," *Molecular and Cellular Biology* 14(2):1054-1065 (1994).

He, Bin et al. "*RAM2*, an essential gene of yeast, and *RAM1* encode the two polypeptide components of the farnesyltransferase that prenylates a-actor and Ras proteins," *Proc. Natl. Acad. Sci. USA* 88:11373-77 (1991).

Hiltunen, J. Kalervo et al. "Peroxisomal Multifunctional β-Oxidation Protein of *Saccharomyces cerevisiae*," *J. of Biol. Chem.* 267(10):6646-6653 (1992).

Hitzeman, R.A. et al., "Use of heterologous and homologous signal sequences for secretion of heterologous proteins from yeast," *Methods Enzymol.* 185:421-40 (1990).

Hrycyna, Christine A. et al. "The *Saccharomyces cerevisiae* STE14 gene encodes a methyltransferase that mediates C-terminal methylation of a-factor and RAS Proteins," *The EMBO J.* 10(1):1699-1709 (1991).

Huang, Chi-Ying F. et al. "Ultrasensitivity in the mitogen-activated protein kinase cascade," *Proc. Natl. Acad. Sci. USA* 93:10078-10083 (1996).

Hughes, David A. et al. "Complementation of *byr1* in fission yeast by mammalian MAP kinase kinase requires coexpression of Raf kinase," *Nature* 364:349-52 (1993).

Inouye, Carla et al. "Ste5 RING-H2 Domain: Role in Ste4-Promoted Oligomerization for Yeast Pheromone Signaling," *Science* 278:103-106 (1997).

Jabbar, M. Abdul et al. "Influenza Viral (A/WSN/33) hemagglutinin is expressed and glycosylated in the yeast *Saccharomyces cerevisiae*," *Proc. Natl. Acad. Sci. USA* 82:2019-23 (1985).

Jakobs, K. H. et al. "Dual regulation of adenylate cyclase. A signal transduction mechanism of membrane receptors," *Basic Res. Cardiol.* 81:1-9 (1986).

Jarvis et al., "Identification of a DNA segment that is necessary and sufficient for alpha-specific gene control in *Saccharomyces cerevisiae*: implications for regulation of alpha-specific and a-specific genes," *Mol. Cell. Biol.* 8(1):309-20 (1988).

Journot, Laurent et al. "Amino Acids 367-376 of the $G_s$ α subunit induce membrane association when fused to soluble amino-terminal deleted $G_{i1}$ a subunit," *Proc. Natl. Acad. Sci. USA* 88:10054-58 (1991).

Julius, David et al. "Glycosylation and Processing of Prepro-α-Factor through the Yeast Secretory Pathway," *Cell* 36:309-18 (1984).

Julius, David et al. "Isolation of the Putative Structural Gene for the Lysine-Arginine-Cleaving Endopeptidase Required for Processing of Yeast Prepro-α-factor," *Cell* 37:1075-89 (1984).

Julius, David et al. "Yeast α Factor is Processed from a Larger Precursor Polypeptide: The Essential Role of a Membrane-Bound Dipeptidyl Aminopeptidase," *Cell* 32:839-52 (1983).

Kaiser, Chris A. et al. "Many Random Sequences Functionally Replace the Secretion Signal Sequence of Yeast Invertase," *Science* 235:312-17 (1987).

Kang, Yoon-Se et al. "Effects of expression of mammalian Gα and hybrid mammalian-yeast Gα proteins on the yeast pheromone response signal transduction pathway," *Molecular and Cellular Biology* 10(6):2582-90 (1990).

King, Klim et al. "Control of Yeast Mating Signal Transduction by a Mammalian $β_2$-Adrenergic Receptor and $G_s$ α Subunit," *Science* 250:121-23 (1990).

Kingsman, S.M. et al. "*The production of mammalian protein in Saccharomyces cerevisiae*," *Tibtech* 5:53-57 (1987).

Koff, Andrew et al. "Human Cyclin E, A New Cyclin That Interacts with Two Members of the *CDC2* Gene Family," *Cell* 66:1217-28 (1991).

Kosugi, Shinji et al. "Characterization of heterogeneous mutations causing constitutive activation of the luteinizing hormone receptor in familial male precocious puberty," *Human Molecular Genetics* 4(2):183-88 (1995).

Kramer, R. A. et al. "HTLV-III *gag* Protein Is Processed in Yeast Cells by the Virus *pol*-Protease," *Science* 231:1580-85 (1986).

Kuchler, Karl and Thorner, Jeremy "Functional expression of human *mdr1* in the yeast *Saccharomyces cerevisiae*," *Proc. Natl. Acad. Sci. USA* 89:2302-06 (1992).

Kuchler, Karl et al. "*Saccharomyces cerevisiae* STE6 gene product: a novel pathway for protein export in eukaryotic cells," *The EMBO J.* 8(13):3973-84 (1989).

Kurjan, "Alpha-factor structural gene mutations in *Saccharomyces cerevisiae*: effects on alpha-factor production and mating," *Mol. Cell. Biol.* 5(4):787-96 (1985).

Kurjan, Janet and Herskowitz "Structure of a Yeast Pheromone Gene (*MFα*): A Putative α-Factor Precursor Contains Four Random Copies of Mature α-Factor," *Cell* 30:933-43 (1982).

Lambright, David G. et al. "Structural determinants for activation of the α-subunit of a heterotrimeric G protein," *Nature* 369:621-28 (1994).

Leberer, Ekkehard et al. "Dominant-negative mutants of a yeast G-protein β subunit identify two functional regions involved in pheromone signaling," *The EMBO J.* 11(13):4805-13 (1992).

Lee, Ethan et al. The G22A Mutant of $G_{sα}$ Highlights the Requirement for Dissociation of G Protein Subunits, *J. Biol. Chem.* 267(2):1212-18 (1992).

Lemire, Bernard D. et al. "The Mitochondrial Targeting Function of Randomly Generated Peptide Sequences Correlates with Predicted Helical Amphiphilicity," *J. Biol. Chem.* 264(34):20206-12 (1989).

Lew, Daniel J. et al. "Isolation of Three Novel Human Cyclins by Rescue of G1 Cyclin (Cln) Function in Yeast," *Cell* 66:1197-1206 (1991).

Linder, Maurine E. and Gilman, Alfred G. "G Proteins," *Scientific American* 267(1):56-65 (1992).

Linder, Maurine E. et al. "Lipid Modifications of G Protein Subunits: Myristoylation of $G_{oα}$ Increases its Affinity for βγ," *J. Biol. Chem.* 266(7):4654-59 (1991).

Lolait et al., "Extrapituitary expression of the rat V1b vasopressin receptor gene" *P.N.A.S. U.S.A.* 92:6783-6787 (1995).

Lupas, Andrei N. et al. "Do G protein subunits associate via a three-stranded coiled coil?" *FEBS* 314(2):105-08 (1992).

Mackay, Vivian and Manney, Thomas R. "Mutations Affecting Sexual Conjugation and Related Processes in *Saccharomyces cerevisiae*. II Genetic Analysis of Nonmating Mutants," *Genetics* 76:273-88 (1974).

Marengere, Luc E.M. and Pawson, Tony "Structure and function of SH2 domains," *J. Cell Science* Suppl. 18:97-104 (1994).

Markby, David W. et al. "Separate GTP Binding and GTPase Activating Domains of a Gα Subunit," *Science* 262:1895-1901 (1993).

Michaelis, Susan and Herskowitz, Ira "The a-Factor Pheromone of *Saccharomyces cerevisiae* is Essential for Mating," *Molecular and Cellular Biol.* 8(3):1309-18 (1988).

Milano, C.A. et al. "Enhanced Myocardial Function in Transgenic Mice Overexpressing the $β_2$-Adrenergic Receptor," *Science* 264:582-86 (1994).

Mollereau, C. et al., "ORL1, a novel member of the opioid receptor family. Cloning, functional expression and localization," *FEBS Lett.* 341(1):33-8 (1994).

Mumby, Susanne M. et al. "G-Protein α-subunit expression, myristoylation, and membrane association in COS cells," *Proc. Natl. Acad. Sci. USA* 87:728-32 (1990).

Murphy, A.J.M. et al. "Autocrine Stimulation of Yeast through Human G-Coupled Receptors," *J. Cell Biochem.* 18B:224 (1994).

Nakafuku, Masato et al. "Occurrence in *Saccharomyces cerevisiae* of a gene homologous to the cDNA coding for the α-subunit of mammalian G proteins," *Proc. Natl. Acad. Sci. USA* 84:2140-44 (1987).

Nakayama, N. et al. "Common signal transduction system shared by *STE2* and *STE3* in haploid cells of *Saccharomyces cerevisiae*: autocrine cell-cycle arrest results from forced expression of *STE2*," *The EMBO J.* 6(1):249-54 (1987).

Neer, Eva J. et al. "The Amino Terminus of a G Protein α Subunits Is Required for Interaction with βγ," *J. Biol. Chem.* 263(18):8996-9000 (1988).

Noel, Joseph P. et al. "The 2.2 Å crystal structure of transducin-α complexed with GTP-γ-S," *Nature* 366:654-63 (1993).

Noelle, Randolph J. et al. "CD40 and its ligand, an essential ligand-receptor pair for thymus-dependent B-cell activation," *Immunol. Today* 13(11):431-33 (1992).

Nomoto, Satoshi et al. "Regulation of the yeast pheromone response pathway by G protein subunits," *The EMBO J.* 9(3):691-696 (1990).

Nye, Jeffrey S. and Kopan, Raphael "Vertebrate ligands for Notch," *Current Biology* 5(9):966-69 (1995).

Oeda, Kenji et al. "Expression of Rat Liver Cytochrome P-450MC cDNA in *Saccharomyces cerevisiae*," *DNA* 4(3):203-10 (1985).

Ogden, Jill E. et al. "Efficient Expression of the *Saccharomyces cerevisiae PGK* Gene Depends on an Upstream Activation Sequence but Does Not Require TATA Sequences," *Molecular and Cellular Biol.* 6(12):4335-43 (1986).

Price, L.A. et al., "Functional coupling of a mammalian somatostatin receptor to the yeast pheromone response pathway," *Mol Cell Biol.* 15(11):6188-95 (1995).

Pronin, Alexey N. and Gautam, Narasimhan "Interaction between G-Protein β and γ subunit types is selective," *Proc. Natl. Acad. Sci. USA* 89:6220-24 (1992).

Ramer, Sandra W. and Davis, Ronald W. "A dominant truncation allele identifies a gene, *STE20*, that encodes a putative protein kinase necessary for mating in *Saccharomyces cerevisiae*," *Proc. Natl. Acad. Sci. USA* 90:452-456 (1993).

Rarick, Helen M. et al. "A Site on Rod G Protein α Subunit That Mediates Effector Activation," *Science* 256:1031-33 (1992).

Raymond, Martine et al. "Functional Complementation of Yeast *ste6* by a Mammalian Multidrug Resistance *mdr* Gene," *Science* 256:232-34 (1992).

Reed, Randall R. "G Protein Diversity and the Regulation of Signaling Pathways," *The New Biologist* 2(11):957-60 (1990).

Schafer, William R. et al. "Enzymatic Coupling of Cholesterol Intermediates to a Mating Pheromone Precursor and to the Ras Protein," *Science* 249:1133-39 (1990).

Schafer, William R. et al. "Genetic and Pharmacological Suppression of Oncogenic Mutations in *RAS* Genes of Yeast and Humans," *Science* 245:379-85 (1989).

Schärer, E. and Iggo, R. "Mammalian p53 can function as a transcription factor in yeast," *Nucleic Acids Research* 20(7):1539-45 (1992).

Scott, Jamie K. and Smith, George P. "Searching for Peptide Ligands with an Epitope Library," *Science* 249:386-90 (1990).

Sikorski, Robert S. and Hieter, Philip "A System of Shuttle Vectors and Yeast Host Strains Designed for Efficient Manipulation of DNA in *Saccharomyces cerevisiae*," *Genetics* 122:19-27 (1989).

Singh, Arjun et al. "*Saccharomyces cerevisiae* contains two discrete genes coding for the α-factor pheromone," *Nucleic Acids Research* 11(12):4049-63 (1983).

Slepak, Vladlen Z. et al. "Mutational Analysis of G Protein α Subunit $G_{oα}$ Expressed in *Escherichia coli*," *J. Biol. Chem.* 268(2):1414-23 (1993).

Spiegel, Allen M. et al. "The G Protein connection: molecular basis of membrane association," *TIBS* 16:338-41 (1991).

Steube, Klaus et al. "α-Factor-leader-directed secretion of recombinant human-insulin-like growth factor I from *Saccharomyces cerevisiae*," *Eur. J. Biochem.* 198:651-57 (1991).

Stevenson, Brian J. et al. "Constitutive mutants of the Protein Kinase STE11 Activate the Yeast Pheromone Response Pathway in the Absence of the G Protein," *Genes & Development* 6:1293-1304 (1992).

Strubin, Michel and Struhl, Kevin "Yeast and Human TFIID with Altered DNA-Binding Specificity of TATA Elements," *Cell* 68:721-30 (1992).

Struhl, Kevin "Constitutive and Inducible *Saccharomyces cerevisiae* Promoters: Evidence for Two Distinct Molecular Mechanisms," *Molecular and Cellular Biol.* 6(11):3847-53 (1986).

Struhl, Kevin et al. "High-frequency transformation of yeast: Autonomous replication of hybrid DNA molecules," *Proc. Natl. Acad. Sci. USA* 76(3):1035-39 (1979).

Struhl, Kevin and Hill, David E. "Two Related Regulatory Sequences are Required for Maximal Induction of *Saccharomyces cerevisiae his3* Transcription," *Molecular and Cellular Biol.* 7(1):104-10 (1987).

Sullivan, Kathleen A. et al., "Identification of receptor contact site involved in receptor-G protein coupling," *Nature* 330:758-60 (1987).

Teem, John L. et al. "Identification of Revertants for the Cystic Fibrosis ΔF508 Mutation Using STE6-CFTR Chimeras in Yeast," *Cell* 73:335-346 (1993).

Thomas, Thomas C. et al. "G-protein $\alpha_o$ subunit: Mutation of conserved cysteines identifies a subunit contact surface and alters GDP affinity," *Proc. Natl. Acad. Sci. USA* 90:10295-99 (1993).

Tyson, John J. et al. "Chemical kinetic theory: understanding cell-cycle regulation," *Trends In Biochem. Sci.* 21:89-96 (1996).

Walker, John E. et al. "Distantly related sequences in the α-and β-subunits of ATP synthase, myosin, kinases and other ATP-requiring enzymes and a common nucleotide binding fold," *The EMBO J.* 1(8):945-51 (1982).

Waters, M. Gerard et al. "Prepro-α-factor Has a Cleavable Signal Sequence," *J. Biol. Chem.* 263(13):6209-14 (1988).

Whiteway, Malcolm S. et al. "Association of the Yeast Pheromone Response G Protein βγ Subunits with the MAP Kinase Scaffold Ste5p," *Science* 269:1572-1575 (1995).

Whiteway, Malcolm et al. "Genetic Identification of Residues Involved in Association of α and β G-Protein Subunits," *Molecular and Cellular Biol.* 14(5):3223-3229 (1994).

Whiteway, Malcolm et al. "The *STE4* and *STE18* Genes of Yeast Encode Potential β and γ Subunits of the Mating Factor Receptor-Coupled G Protein," *Cell* 56:467-477 (1989).

Xiong, Yue et al. "Human D-Type Cyclin," *Cell* 65:691-99 (1991).

Zervos, Antonis S. et al. "Mxi1, a Protein that Specifically Interacts with Max to Bind Myc-Max Recognition Sites," *Cell* 72:223-32 (1993).

Zhan, Xiao-Li et al. "Differential regulation of *FUS3* MAP kinase by tyrosine-specific phosphatases *PTP2/PTP3* and dual-specificity phosphatase *MSG5* in *Saccharomyces cerevisiae*," *Genes & Development* 11:1690-1702 (1997).

\* cited by examiner

017
SYSTEM FOR DETECTION OF A FUNCTIONAL INTERACTION BETWEEN A COMPOUND AND A CELLULAR SIGNAL TRANSDUCTION COMPONENT

This application is a divisional application of U.S. patent application Ser. No. 09/592,010, filed on Jun. 12, 2000, issued on Apr. 29, 2003 as U.S. Pat. No. 6,555,325, which claims priority to U.S. Provisional Patent Application No. 60/139,021, filed on Jun. 14, 1999. All of the aforementioned applications are incorporated herein in their entireties by this reference.

FIELD OF THE INVENTION

The invention is related to the detection of the transduction of an extracellular signal by an intracellular signal transduction pathway. In particular, the invention relates to methods and compositions useful for identifying a test compound as an agonist or antagonist of a cellular receptor.

BACKGROUND OF THE INVENTION

The identification of biological activity in new molecules has historically been accomplished through the use of in vitro assays or whole animals. Intact biological entities, either cells or whole organisms, have been used to screen for anti-bacterial, anti-fungal, anti-parasitic and anti-viral agents in vitro. Cultured mammalian cells have also been used in screens designed to detect potential therapeutic compounds. A variety of bioassay endpoints have been exploited in cell screens including the stimulation of growth or differentiation of cells, changes in cell motility, the production of particular metabolites, the expression of specific proteins within cells, altered protein function, and altered conductance properties. Cytotoxic compounds used in cancer chemotherapy have been identified through their ability to inhibit the growth of tumor cells in vitro and in vivo. In addition to cultures of dispersed cells, whole tissues have served in bioassays, as in those based on the contractility of muscle.

In vitro testing is a preferred methodology in that it permits the design of high-throughput screens: small quantities of large numbers of compounds can be tested in a short period of time and at low expense. Optimally, animals are reserved for the latter stages of compound evaluation and are not used in the discovery phase, inasmuch as the use of whole animals is labor-intensive and extremely expensive.

The search for agonists and antagonists of cellular receptors has been an intense area of research aimed at drug discovery because of the elegant specificity of these molecular targets. Drug screening has been carried out using whole cells expressing functional receptors and, recently, binding assays employing membrane fractions or purified receptors have been designed to screen compound libraries for competitive ligands.

G protein-coupled receptors (GPCRs) are a particularly important category of cell surface receptors. The medical importance of these receptors is evidenced by the fact that more than 60% of all commercially available prescription drugs work by interacting with known GPCRs. Hundreds, if not thousands, of receptors convey messages through heterotrimeric G proteins, of which at least 17 distinct forms have been isolated. Most G protein-coupled receptors are comprised of a single protein chain that is threaded through the plasma membrane seven times. Such receptors are often referred to as seven-transmembrane receptors (STRs). More than a hundred different GPCRs have been found, including many distinct receptors that bind the same ligand, and there are likely many more GPCRs awaiting discovery. The development of new drug discovery assays to identify novel modulators of GPCRs would be of tremendous benefit.

The heterologous expression of recombinant mammalian G protein-coupled receptors in mammalian cells which do not normally express those receptors has been described as a means of studying receptor function for the purpose of identifying agonists and antagonists of those receptors. For example, the human muscarinic receptor (HM1) has been functionally expressed in mouse cells (Harpold et al. U.S. Pat. No. 5,401,629). The rat V1b vasopressin receptor has been found to stimulate phosphotidylinositol hydrolysis and intracellular $Ca^{2+}$ mobilization in Chinese hamster ovary cells upon agonist stimulation (Lolait et al. (1995) *Proc. Natl. Acad Sci.*USA 92:6783–6787). These types of ectopic expression studies have enabled researchers to study receptor signaling mechanisms and to perform mutagenesis studies which have been useful in identifying portions of receptors that are critical for ligand binding or signal transduction.

Experiments have also been undertaken to express functional G protein-coupled receptors in yeast cells. For example, U.S. Pat. No. 5,482,835 to King et al describes a transformed yeast cell which is incapable of producing a yeast G protein cc subunit, but which has been engineered to produce both a mammalian G protein α-subunit and a mammalian receptor which is "coupled to" (i.e., interacts with) the aforementioned mammalian G protein cc-subunit. Specifically, U.S. Pat. No. 5,482,835 reports expression of the human beta-2 adrenergic receptor (β2AR), a seven transmembrane receptor (STR), in yeast, under control of the GAL1 promoter, with the β2AR gene modified by replacing the first 63 base pairs of coding sequence with 11 base pairs of noncoding and 42 base pairs of coding sequence from the STE2 gene. (STE2 encodes the yeast α-factor receptor.) It was found that the modified β2AR was functionally integrated into the membrane, as shown by studies of the ability of isolated membranes to interact properly with various known agonists and antagonists of β2AR. The ligand binding affinity for yeast-expressed β2AR was said to be nearly identical to that observed for naturally produced β2AR.

U.S. Pat. No. 5,482,835 also describes co-expression of a rat G protein α-subunit in yeast strain 8C, which lacks the cognate yeast protein. Ligand binding resulted in G protein-mediated signal transduction. U.S. Pat. No. 5,482,835 further teaches that these cells may be used in screening compounds for the ability to affect the rate of dissociation of Gα from Gβγ in a cell. For this purpose, the cell further contains a pheromone-responsive promoter (e.g., BAR1 or FUS1), linked to an indicator gene (e.g. HIS3 or lacZ). The cells are placed in multi-titer plates, and different compounds are placed in each well. The colonies are then scored for expression of the indicator gene. DNA vectors and host yeast cells for use in the method are also disclosed (see U.S. Pat. No. 5,739,029).

U.S. Pat. No. 5,789,184 describes yeast cells engineered to express a heterologous kinase as a yeast pheromone system protein surrogate, and a heterologous polypeptide. The yeast cells are used in assays to screen for peptides that modulate the activity of non-yeast surrogates.

U.S. Pat. No. 5,879,591 describes yeast cells engineered to express a heterologous protein (e.g., a farnesyl transferease) which functions as a surrogate for, and performs the function of, a yeast pheromone system protein, as well as a heterologous polypeptide. The yeast cells are useful in screening assays to identify polypeptides which modulate the interaction of the surrogate with the yeast pheromone system.

U.S. Ser. No. 08/322,137 describes yeast cells engineered to express both a surrogate, e.g., a G protein-coupled receptor, of a pheromone pathway component and a potential peptide modulator of the surrogate. This is performed in such a manner that inhibition or antagonism of the surrogate by the peptide modulator affects a screenable or selectable trait of the yeast cell. Also included are mechanisms by which the signal-to-noise ratio of the system may be improved. The yeast cells are useful in assays to screen for peptides that modulate the activity of endogenous and heterologous yeast pheromone system surrogates.

Published PCT international application WO 98/13513 describes methods for identifying modulators of heterologous receptors expressed in yeast. Modulators are identified by detecting an alteration in a signal produced by an endogenous yeast signaling pathway.

Published PCT international application WO 99/18211 describes novel yeast cells which express a heterologous G protein coupled receptor and mutant and/or chimeric G protein subunit molecules which serve to functionally integrate the heterologous receptor into the pheromone signaling pathway of the yeast cell.

SUMMARY OF THE INVENTION

It is an object of the present invention to provide a novel, rapid, reproducible, robust assay system for screening and identifying pharmaceutically effective compounds that specifically interact with and modulate the activity of a cellular receptor or ion channel of a cell. More particularly, the invention provides a highly sensitive assay system for the identification of agonist or antagonist activity of a test compound for a specific receptor.

Thus, in one aspect, the invention provides a method for identifying a test compound that modulates a heterologous receptor in a cell. The method comprises providing a first cell containing a heterologous receptor that is functionally integrated into a first signal transduction pathway of this first cell, where a signal molecule is produced by the first cell upon activation of the first signal transduction pathway; and providing a second cell which is responsive to production of the signal molecule by the first cell, such that a detectable signal is generated by the second cell in response to production of the signal molecule by the first cell. Upon contacting the first cell with the test compound, modulation of the heterologous receptor by the test compound is indicated by generation of the detectable signal by the second cell.

For example, a first cell, termed the 'test' cell, containing a desired receptor (either native or heterologous) which is functionally coupled to a first signal transduction pathway, is challenged with a test compound. If the test compound has a stimulatory (agonist) effect upon the receptor, a signal will be transmitted through the coupled signal transduction pathway; resulting in production (e.g., secretion) of a signal molecule by the test cell. The signal compound stimulates a second "detector" cell. The detector cell is responsive to (e.g., by expressing receptors for) the signal molecule. In one embodiment, the detector cell expresses a receptor for the signal molecule such that upon binding of the signal molecule, a second signal is transmitted through a second pathway functionally coupled to this second receptor. Stimulation of this second pathway in the detector cell can be measured either by some factor intrinsic to this second pathway, or more conveniently, by the inclusion of a reporter gene coupled to the pathway. Thus, signaling through the pathway stimulates the expression of a reporter molecule which confers a detectable phenotype upon the detector cell (such as a colorimetric, luminescent, or growth phenotype). The test and detector cells may be in mixed culture, may be separated by a semipermeable membrane, or may be entirely separate, with only the extracellular material from the test cell culture contacted with the detector cells.

In a preferred embodiment, the present invention provides a novel and sensitive alpha factor readout assay to assess the signal transduction activity through the pheromone response pathway in yeast cells. In this embodiment, a MATα yeast test cell, containing a heterologous G-protein coupled receptor (GPCR), is stimulated with a ligand of the GPCR. If reactive with the ligand, this stimulation results in increased α-factor expression and secretion; the amount of α-factor secretion is indicative of the activity of the pheromone signaling pathway in the test cell. The secreted α-factor binds to an α-factor receptor on a second, detector yeast cell of MATa mating type. Upon binding of α-factor, the pheromone response pathway in this detector cell is activated. The detector cell may also include an indicator gene (such as lacZ) operatively linked to a promoter sensitive to upregulation of this second pathway (such as FUS1), such that the readout from the indicator gene yields a determination of the quantity of α-factor present. Alternatively, a growth readout may be used, wherein expression of the indicator gene (such as LEU2) corrects for an auxotrophy and permits growth of the detector cells on selective medium.

The invention also provides methods by which the sensitivity of the assay may be increased. In one embodiment, for example, the invention provides for the elimination of constitutive background expression and secretion of α-factor in an *S. cerevisiae* test cell by inactivation of the MFα1 gene in order to improve the detection limits of the assay. In other embodiments, the detector cell also comprises one or more gene mutations, the effect of which is to increase significantly the sensitivity of the response of the second pathway to receptor-dependent activation.

In another embodiment, the invention provides a method for identifying a compound that modulates production of a gene product produced by a cell. The method comprises providing a first cell, the first cell containing a surrogate of a signal transduction pathway of the first cell, where a gene product is produced by the surrogate upon activation of the signal transduction pathway, and also providing a second cell having means for generating a detectable signal and being responsive to the gene product, such that a detectable signal is generated by the second cell in response to stimulation of the second cell by the gene product, and contacting the first cell with a test compound; whereby the modulation is indicated by generation of the detectable signal by the second cell.

In another aspect, the invention is directed to a method for detecting a gene product produced by a cell. The method comprises causing a signal to be transmitted through a signal transduction pathway of a first cell, such that a gene product is produced by the first cell upon transmission of the signal through the signal transduction pathway; and detecting the gene product by means of a second cell which is responsive to the gene product produced by the first cell, where the second cell generates a detectable signal in response to production of the gene product by the first cell. In a preferred embodiment, the method further comprises providing a first cell, this first cell containing a surrogate of a signal transduction pathway of the first cell, where a gene product is produced by the surrogate upon activation of the signal transduction pathway; and also providing a second cell, this second cell having means for generating a detectable signal, such that a detectable signal is generated by the second cell in response to stimulation of the second cell by the gene product. In a particularly preferred embodiment, the signal transduction pathway is a yeast pheromone response pathway.

Yet another aspect of the invention is directed to recombinant cells. In one embodiment, the invention provides a recombinant cell comprising a surrogate of a signal transduction pathway of said cell, where a signal molecule is produced by the surrogate upon activation of the signal transduction pathway, and where production of the signal molecule is capable of detection by a second cell having means for generating a detectable signal, such that a detectable signal is generated by the second cell in response to stimulation of the second cell by the signal molecule. In a preferred embodiment, the signal transduction pathway is a yeast pheromone response pathway. In another preferred embodiment, the signal molecule is a gene product, with a natural product being particularly preferred.

In another embodiment, the invention provides a mixture of recombinant cells comprising a first recombinant cell and a second recombinant cell, where the first cell contains a surrogate of a signal transduction pathway of the cell, such that a signal molecule is produced by the surrogate upon activation of the signal transduction pathway, and where the second cell contains means for generating a detectable signal such that a detectable signal is generated by the second cell in response to stimulation of the second cell by the signal molecule.

In yet another embodiment, the invention provides a mixture of recombinant cells comprising a first recombinant cell and a second recombinant cell, where the first cell contains a heterologous receptor that is functionally integrated into a signal transduction pathway of the first cell, and produces a signal molecule upon activation of this signal transduction pathway, and where the second cell contains means for generating a detectable signal, and is responsive to the signal molecule produced by the first cell, such that a detectable signal is generated by the second cell in response to production of the signal molecule by the first cell.

In another aspect, the present invention provides a kit for screening of test compounds that modulate a heterologous receptor in a cell. This kit comprises a first cell having a heterologous receptor that is functionally integrated into a first signal transduction pathway of this first cell; a signal molecule is produced by this first cell upon activation of the first signal transduction pathway. This kit also comprises a second cell which is responsive to production of the signal molecule by the first cell, such that a detectable signal is generated by the second cell in response to production of the signal molecule by the first cell.

DETAILED DESCRIPTION OF THE INVENTION

Figure 1:
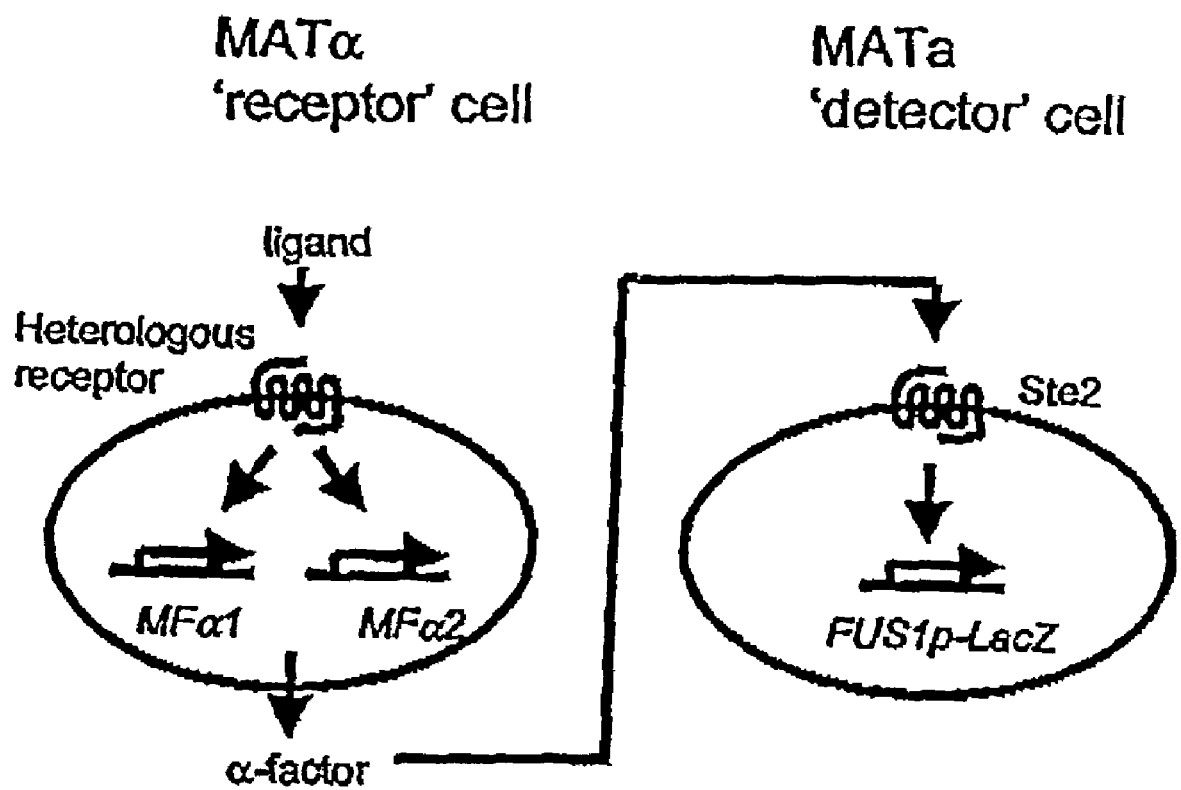
FIG. 1 is a schematic diagram of the invention assay applied to the detection of activity of the pheromone receptor pathway in yeast cells.

Proliferation, differentiation and death of eukaryotic cells are controlled by a variety of extracellular signals, such as hormones, neurotransmitters, and polypeptide factors. These diffusible ligands allow cells to influence and be influenced by environmental cues. The study of receptor-ligand interaction has revealed a great deal of information about how cells respond to external stimuli, and this knowledge has led to the development of therapeutically important compounds.

The present invention makes available a rapid, effective assay for screening and identifying pharmaceutically effective compounds that specifically interact with and modulate the activity of a cellular receptor, ion channel, or a surrogate of a pheromone response pathway component. The subject assay enables rapid screening of large numbers of compounds including, for example, small organic molecules, or polypeptides in an expression library to identify compounds which induce or antagonize receptor bioactivity.

The assay of the present invention provides a convenient format for discovering drugs which can be useful to modulate cellular function, as well as to understand the pharmacology of compounds that specifically interact with cellular receptors, ion channels, and components that modulate a surrogate of the pheromone response pathway, e.g., kinases, farnesyl transferases, and ABC transporters. Moreover, the subject assay is particularly amenable to identifying ligands, natural or artificial, for receptors and ion channels.

I. Definitions

Before further description of the invention, certain terms employed in the specification, examples and appended claims are, for convenience, collected here.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express a reporter gene construct, heterologous receptor or test polypeptide.

The terms "operatively linked", "operably linked", and "associated with" are used herein interchangeably and are intended to mean that molecules are functionally coupled to each other in that the change of activity or state of one molecule is affected by the activity or state of the other molecule. Typically, two polypeptides are covalently attached through peptide bonds.

The terms "protein", and "polypeptide" are used interchangeably herein. The term "peptide" is used herein to refer to a chain of two or more amino acids or amino acid analogs (including non-naturally occurring amino acids), with adjacent amino acids joined by peptide (—NHCO—) bonds. Thus, the peptides of the invention include oligopeptides, polypeptides, proteins, and peptidomimetics. Methods for preparing peptidomimetics are known in the art. In particular, a peptidomimetic can be derived as a retro-inverso analog of the peptide. Such retro-inverso analogs can be prepared according to methods known in the art (see, e.g., U.S. Pat. No. 4,522,752).

The term "receptor" as used herein refers to a protein expressed by a cell for the purpose of serving as a docking site for a signal molecule. Receptors are able to interact both with a signal molecule and also with one or more signal transduction pathways; by binding to or specifically interacting with a signal molecule, the receptor is able to modulate signaling through the signal transduction pathway to which it is functionally coupled. Examples of such receptors include, but are not limited to, G-protein coupled receptors and ion channels. Also included in this term are nonproteinaceous molecules utilized by a cell to act as docking sites for a signal molecule, such as lipid molecules.

The term "responsive" as used herein refers to an alteration in the detector cell upon exposure to a signal molecule. Such alteration is preferably detectable, as in the expression of an indicator molecule or a growth phenotype, but also encompasses genotypic or other changes which are detectable only with more extensive assays, such as modulation of transcription of a particular gene.

The term "contacting" as used herein refers to exposure of a cell to a test compound or signal molecule for a sufficient duration of time and in a sufficient quantity such that the cell may respond to the presence of the compound. Contacting may occur via binding of the compound to a receptor, but this term is not limited to such an activity; any interaction of the cell with the test compound is meant to be incorporated by this term.

The term "indicator molecule" as used herein refers to a polypeptide which provides a detectable signal, for example, green fluorescent protein (GFP).

The term "activation" (as in "activation" of a pheromone response/signal transduction pathway of a yeast cell") is intended to refer to "switching on" the signal transduction cascade. The signal transduction cascade can be switched on by external signals that interact with cell receptors, e.g., ligand binding to a G protein-coupled receptor. The term "stimulation" is also intended to encompass switching on the signal transduction cascade by any other process including, for example, a process similar to the process by which phorbol esters activate the calcium dependent signal transduction pathway of T cell receptors.

The term "functionally integrated" (as in a receptor that is "functionally integrated into a signal transduction pathway in a cell" or "functionally integrated into a yeast pheromone response pathway") is intended to refer to the ability of the receptor to be expressed at the surface of the cell and the ability of the expressed receptor to bind to modulators (e.g., a ligand of the receptor) and transduce signals into the cell via components of a signal transduction pathway of the cell. For example, a G protein-coupled receptor (GPCR) which is functionally integrated into an endogenous pheromone response pathway of a yeast cell is expressed on the surface of the yeast cell, couples to a G protein of the pheromone response pathway within the yeast cell, and transduces a signal in that yeast cell upon binding of a modulator to the receptor.

The term "modulation" is intended to encompass, in its various grammatical forms (e.g., "modulated", "modulation", "modulating", etc.), up-regulation, induction, stimulation, potentiation, localization changes (e.g., movement of a protein from one cellular compartment to another) and/or relief of inhibition, as well as inhibition and/or down-regulation.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation. A "signal transduction pathway" refers to the components involved in "signal transduction" of a particular signal into a cell. The term "endogenous signal transduction pathway" indicates that some or all of the components of the signal transduction pathway are naturally-occurring components of the cell. An example of such a pathway is the endogenous pheromone response pathway of yeast.

The term "signal transduction pathway surrogate" or "pathway surrogate" as used herein is intended to encompass heterologous molecules and proteins which are able to functionally couple with an existing signal transduction pathway of the cell such that the pathway remains functional. Frequently, the incorporation of a pathway surrogate requires the selective removal of one or more native molecules, which can be accomplished by methods known in the art, for example, by a genetic knockout.

The term "signal molecule" as used herein is intended to encompass molecules and changes in the environment produced as a result of transduction of a signal through a signal transduction pathway. Such production can be direct or indirect, but in either case, the production of the signal molecule is an indicator that signaling through said signal transduction pathway has taken place. Signal molecules in accordance with the invention include, but are not limited to, polypeptides expressed upon signaling through the pathway, and small organic or inorganic molecules, such as oxygen radicals or ions. Emission of light or heat in response to signaling through a cellular pathway is also encompassed by this term.

The term "detecting an alteration in a signal produced by a signal transduction pathway" (e.g., a yeast pheromone response pathway) is intended to encompass the detection of alterations in second messengers produced upon activation of components of the signal transduction pathway, alterations in gene transcription induced upon activation of components of the signal transduction pathway, and/or alterations in the activity of a protein(s) upon activation of components of the signal transduction pathway. In some embodiments, the term "detecting an alteration in a signal produced by an endogenous signal pathway" is not, however, intended to encompass detecting alterations in the level of expression of an exogenous reporter gene that has been introduced into the cell or the activity of the reporter gene product. Moreover, the term "detecting an alteration in a signal produced by a signal transduction pathway" is not intended to encompass assaying general, global changes to the cell. Rather, this term indicates that a specific signal associated with the signal transduction pathway is assayed.

As used herein, the term "extracellular signal" is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels. The term, "extracellular signal" also includes as yet unidentified substances that modulate the activity of a cellular receptor, and thereby influence intracellular fuctions. Such extracellular signals are potential pharmacological agents that may be used to treat specific diseases by modulating the activity of specific cell surface receptors.

The term "wild type protein" as used herein refers to unmodified, naturally occurring cellular proteins (e.g., a yeast protein) or fragments thereof The term "mutated protein" or "mutant protein" as used herein refers to a cellular proteins (e.g., a yeast protein), or fragment thereof, that has been modified by addition, deletion or substitution of amino acid residues in the protein. Preferably, the mutated protein is derived from the wild type protein.

The term "compound" as used herein (e.g., as in "test compound") is meant to include both exogenously added test compounds and peptides endogenously expressed from a peptide library. For example, in certain embodiments, the reagent cell also produces the test compound which is being screened. The reagent cell can produce, e.g., a test polypeptide, a test nucleic acid and/or a test carbohydrate which is screened for its ability to modulate the receptor/channel activity. In such embodiments, a culture of such reagent cells will collectively provide a library of potential effector molecules and those members of the library which either agonize or antagonize the receptor or ion channel function can be selected and identified. Moreover, it will be apparent that the reagent cell can be used to detect agents which transduce a signal via the receptor or channel of interest.

In other embodiments, the test compound is exogenously added. In such embodiments the test compound is contacted with the reagent cell. Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

The term "non-peptidic compound" is intended to encompass compounds that are comprised, at least in part, of molecular structures different from naturally-occurring L-amino acid residues linked by natural peptide bonds of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds, for example small organic molecules. "Non-peptidic compounds" also are intended to include natural products.

The term "receptor effector" is intended to include agonists and antagonists that modulate signal transduction via a receptor. Receptor effector molecules are capable of binding to the receptor, though not necessarily at the binding site of the natural ligand. Receptor effectors can modulate signal transduction when used alone, i.e. can be surrogate ligands, or can alter signal transduction in the presence of the natural ligand, either to enhance or inhibit signaling by the natural ligand. The term "antagonists" as used herein refers to molecules that block or decrease the signal transduction activity of a receptor; e.g., they can competitively, non competitively, and/or allosterically inhibit signal transduction from the receptor.

The term "agonist" as used herein refers to agents which: induce activation of receptor signaling pathways, e.g., such as by mimicking a ligand for the receptor; potentiate the sensitivity of the receptor to a ligand, e.g., lower the concentrations of ligand required to induce a particular level of receptor-dependent signaling; or otherwise enhance the signal transduction activity of a receptor.

The terms "receptor activator" and "surrogate ligand" as used herein refer to an agonist which induces signal transduction from a receptor.

"Orphan receptor" is a designation given to a receptor for which no specific natural ligand has been described and/or for which no function has been determined.

The term "endogenous gene" is intended to refer to a gene in a cell that is naturally part of the genome of the cell and which, most preferably, is present in its natural location in the genome (as opposed to "heterologous" DNA which has been introduced into the cell). Likewise, the term "endogenous protein" is intended to include proteins of a cell that are encoded by endogenous genes of the cell.

The term "gene product" as used herein is intended to encompass natural products and non-natural products produced directly or indirectly by transcription of a gene as the result of transduction of a signal through a signal transduction pathway, including, but are not limited to, polypeptides, small organic molecules, inorganic molecules, such as oxygen radicals or ions, and the emission of light or heat. In certain embodiments, gene products include endogenous proteins expressed by genes native to a cell, as well as heterologous proteins expressed by heterologous genes or native genes which have been mutated.

The term "heterologous promoter" as used herein, refers to a promoter that does not naturally regulate the gene to which the heterologous promoter is operatively linked. For example, an endogenous yeast gene that is not normally responsive to a signal transduction pathway of the yeast cell (e.g., a yeast pheromone response pathway) can be operatively linked to a heterologous promoter, also not normally responsive to signals produced by the transduction pathway. A fusion protein of the invention, which is engineered to be responsive to the signal transduction pathway, is used to confer signal transduction responsiveness to the endogenous yeast gene through association of the binding site of the heterologous promoter with a region of the fusion protein.

The term "indicator gene" as used herein refers to an expressible (e.g., able to be transcribed and (optionally) translated) DNA sequence which is expressed in response to activation of the fusion protein of the invention. Exemplary indicator genes include unmodified endogenous genes operatively linked to heterologous promoters.

The terms "reporter gene" and "reporter gene construct" are used interchangeably herein to refer to an indicator gene operatively linked to at least one transcriptional regulatory sequence. Transcription of the reporter gene is controlled by the transcriptional regulatory sequence to which it is operatively linked. Exemplary transcriptional control sequences are promoter sequences. Examples of promoters include, but are not limited to, Gal1, Gal10, Mel and LexA operator. The activity of at least one or more of these control sequences is dependent on the activity of a fusion protein of the current invention, in contrast to the natural pheromone regulation of the reporter genes known in the art, (e.g., Fus1-lacZ, Fus1-HIS3, etc.; see, e.g., U.S. Pat. Nos. 5,401,629 and 5,691, 188). A reporter gene is also meant to include a promoter-reporter gene construct which is heterologously expressed in a cell.

The terms "transcriptional control element" and "transcriptional regulatory element" are used interchangeably herein, and are intended to encompass any moiety which controls/regulates transcription of a gene to which it is operatively linked, including, but not limited to, promoters, operators and enhancers which are responsive to signal transduction pathways.

As used herein, "heterologous DNA" or "heterologous nucleic acid" includes DNA that does not occur naturally as part of the genome in which it is present, or which is found in a location or locations in the genome that differs from that in which it occurs in nature. Heterologous DNA is DNA that is not naturally occurring in that position or is not endogenous to the cell into which it is introduced, but has been obtained from another cell. Generally, although not necessarily, such DNA encodes proteins that are not normally produced by the cell in which it is expressed. Heterologous DNA can be from the same species, although in preferred embodiments, it is from a different species. In particularly preferred embodiments, it is mammalian, e.g., human. Heterologous DNA may also be referred to as foreign DNA. Any DNA that one of skill in the art would recognize or consider as heterologous or foreign to the cell in which it is expressed is herein encompassed by the term heterologous DNA. Examples of heterologous DNA include, but are not limited to, DNA that encodes test polypeptides, receptors, reporter genes, transcriptional and translational regulatory sequences, or selectable or traceable marker proteins, such as a protein that confers drug resistance.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

To determine the percent homology of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). For example, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* (48):444–453 (1970)) algorithm which has been incorporated into the GAP program in the GCG software package (available at http:H/www.gcg.com), using either a Blossom 62 matrix or a PAM250 matrix, and a gap weight of 16, 14, 12, 10, 8, 6, or 4, and a length weight of 1, 2, 3, 4, 5, or 6. In another embodiment, the percent identity between two nucleotide sequences is determined using the GAP program in the GCG software package (available at http://www.gcg.com), using a NWSgapdna.CMP matrix and a gap weight of 40, 50, 60, 70, or 80, and a length weight of 1, 2, 3, 4, 5, or 6. In another embodiment, the percent identity between two amino acid or nucleotide sequences is determined using the algorithm of E. Meyers and W. Miller (*CABIOS,* 4:11–17 (1989)) which has been incorporated into the ALIGN program (version 2.0), using a PAM120 weight residue table, a gap length penalty of 12, and a gap penalty of 4.

The nucleic acid and protein sequences of the present invention can further be used as a "query sequence"to perform a search against public databases to identify, for example, other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes. A "heterologous receptor" is a specific embodiment of a "heterologous protein", wherein the heterologous receptor is encoded by heterologous DNA and, upon expression of this heterologous DNA in a recombinant cell, the heterologous receptor is expressed in the recombinant cell.

The term "means for generating a detectable signal" is intended to encompass any molecule, cellular component, system or construct that enables a cell to generate a detectable signal in response to an internal or external stimulus, including, but not limited to, indicator molecules, indicator genes, reporter genes, promoter-reporter gene constructs and the like.

The term "surrogate" as in "surrogate of a signal transduction pathway" or "pathway surrogate" as used herein is intended to encompass heterologous molecules and proteins which are able to substitute for endogenous components of an signal transduction pathway of a cell and/or couple functionally with a signal transduction pathway of a cell such that the pathway remains functional. Frequently, the incorporation of a pathway surrogate requires the selective removal of one or more native molecules, which can be accomplished, for example, by a genetic knockout.

The term "pheromone system protein surrogate" (abbreviated as "PSP surrogate") is intended to refer to a heterologous protein in a yeast cell which is functionally homologous to a yeast protein of the pheromone response pathway (i.e., the PSP surrogate is functionally integrated into the yeast pheromone system pathway). Examples of PSP surrogates, and methods of preparing yeast cells comprising such PSP surrogates, are described in detail in PCT Publication WO 94/23025. Preferred PSP surrogates include G protein-coupled receptors, G proteins, proteases, kinases, farnesyl transferases, carboxymethyl transferases, ABC transporters and cyclins.

The term "autocrine cell", as used herein, refers to a cell which produces a substance which can stimulate a receptor located on or within the same cell as that which produces the substance. For example, wild-type yeast MATα and MATa cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) and also express the receptor are called "autocrine cells". In some instances, such cells can also be referred to as "putative autocrine cells" since some of the cells will express peptides from the library which will not activate the receptor which is expressed. In a library of such cells, in which a multitude of different peptides are produced, it is likely that one or more of the cells will be "autocrine" in the stricter sense of the term.

II. Overview of Assay

In accordance with one embodiment of the assay of the invention, a first cell, termed the "test" cell, is stimulated through contact with a test compound, that interacts with a particular receptor that is either endogenous to the test cell or expressed in the test cell by genetic manipulations well known in the art. Upon stimulation, this receptor transmits a signal, either indirectly through a signal transduction pathway to which it is functionally coupled (as in the case of a cell surface receptor), or directly through the promotion or repression of gene expression (as in the case of an intracellular receptor). The outcome in either case is the production by the test cell of a signal compound (e.g., a secreted protein).

The signal molecule produced by the first cell stimulates a second cell, termed the "detector" cell. The second cell is "responsive" to the signal molecule produced by the first cell. For example, the detector cell can express natural receptors for the signal molecule, and upon binding of the compound, a signal is transmitted though a pathway functionally coupled to these receptors. Stimulation of this pathway can be measured either by some factor intrinsic to this pathway, or more conveniently, by the inclusion in the detector cell of a means for generating a detectable signal, e.g., a reporter gene coupled to the pathway such that signaling through the pathway stimulates the expression of the reporter molecule which can be readily quantified.

The test and detector cells may be in mixed culture, may be separated by a semipermeable membrane, or may be entirely separate, with only the extracellular material from the test cell culture contacted with the detector cell. Standard control experiments are advantageously performed, such as quantitation of the amount of detectable signal generated by the detector cell with the text cell is not challenged with the test compound, or when the test cell is challenged by the test compound but lacks the target receptor.

The activation of various signal transduction pathways in budding yeast or other eukaryotic organisms can lead to the production of gene products and other natural products (e.g., in budding yeast, stimulation of the high osmolarity glycerol response pathway by conditions of high osmolarity results in the increased production of glycerol). Such gene products or natural products may be used to monitor the extent of signaling through the signal transduction pathway, as described herein. Second, if a library of random peptides is expressed in either the detector cell or the test cell, an enrichment in peptides which stimulate the heterologous receptor can be achieved. Isolation from yeast cells of the plasmid DNA encoding the stimulating peptide can occur after one or more rounds of enrichment followed by testing of purified single colonies. This process/method can be used to isolate plasmids encoding peptides of specific sequences which are functional in modulating the desired signal transduction pathway.

In a preferred embodiment, the present invention provides a novel and sensitive α-factor readout assay to assess the signal transduction activity through the pheromone response pathway in yeast. In accordance with this embodiment, a MATα yeast test cell, containing a heterologous G protein-coupled receptor (GPCR), is contacted with a putative ligand ("the test compound") of the GPCR. If reactive with the ligand, the receptor stimulates increased α-factor expression and secretion by the cell. The amount of α-factor secretion is indicative of the activity of the pheromone signaling pathway in the test cell, thus indicating the ability of the test compound to activate the receptor expressed in the test cell. The secreted α-factor binds to the natural α-factor receptor on a second, detector yeast cell of MATa mating type. Upon binding of α-factor, the pheromone response pathway in this detector cell is activated.

The detector cell includes a means for generating a detectable signal upon activation of the pheromone response pathway. In a preferred embodiment, the detector cell includes an indicator gene-(e.g., lacZ) operatively linked to a pheromone responsive promoter (e.g., FUS1), such that the readout or detectable signal produced by the indicator gene yields a determination of the quantity of α-factor present.

Further, it is possible to detect signaling in *S cerevisiae* and related yeast strains not only of the pheromone response pathway, but also of signal transduction pathways which are functionally coupled to the pheromone response pathway, either naturally or by genetic engineering. Examples of such signal transduction pathways include the high osmolarity glycerol (HOG) pathway, and the pseudohyphal/invasive growth pathway (O' Rourke, S. M. and Herskowitz, I. (1998) *Genes Dev.* 12 (18): 2874–2886; Banuett, F. (1998) *Microbiol. Mol. Biol. Rev.* 62 (2): 249–274). MAP kinase cascades are also known to be interconnected with the pheromone response pathway (Herskowitz, I. (1995) *Cell* 80 (2): 187–197). Thus, signaling by a native or heterologous receptor which is functionally coupled to one such non-pheromone response pathway may still be detected through the secretion of α-factor.

In another embodiment of the invention a heterologous receptor can be expressed in the test cell and the detector cell can express a mating factor-inducible reporter gene that confers a growth phenotype to the detector cell and/or its neighboring cells. If a library of random peptides is expressed in either the detector cell or the test cell, an enrichment in peptides that stimulate the heterologous receptor can be achieved. Isolation from yeast cells of the plasmid DNA encoding the stimulating peptide can occur after one or more rounds of enrichment followed by testing of purified single colonies.

The present invention also provides means by which the sensitivity of the assay may be increased. In one embodiment in which a *S. cerevisiae* yeast cell is used as the test cell, the constitutive background expression and secretion of α-factor in the test cell is advantageously eliminated by the inactivation, by, e.g., deletion or mutation, of the MFα1 gene to provide enhanced sensitivity. In another embodiments, the detector cell contains an indicator gene fused to a signal transduction-responsive promoter, e.g., the FUS1 promoter in the case of the pheromone response pathway. In still other embodiments, the detector cell also comprises one or more gene mutations, the effect of which is to greatly increase the sensitivity of the response of the cell to receptor-dependent activation of the pheromone response pathway.

In another aspect, the invention provides a kit for screening of test compounds that modulate a heterologous receptor in a cell. The kit includes a first cell which comprises a heterologous receptor that is functionally integrated into a first signal transduction pathway of the first cell, wherein a signal molecule is produced by the first cell upon activation of the first signal transduction pathway; and a second cell which comprises a receptor for the signal molecule, wherein the receptor is functionally integrated into a second signal transduction pathway of the second cell such that a detectable signal is generated upon activation of the second signal transduction pathway. The kit also includes materials such as growth media, buffers appropriate for the introduction of test compounds, and reagents for quantitating the amount of detectable signal generated, and instructional materials for carrying out the screening assay. In a preferred embodiment, the invention provides a kit for the screening of potential agonist or antagonist compounds for a desired GPCR, including a first, MATα yeast cell (the test cell) containing an MFα1 deletion, to be transformed with a GPCR of choice. The kit also includes a second, MATa yeast cell (the detector cell), containing an indicator gene operatively linked to the pheromone pathway-upregulated promoter, such as FUS1.

The present invention provides for the use of any type of cell in the subject assays, whether prokaryotic or eukaryotic. In preferred embodiments, the cells of the present invention are eukaryotic. In certain preferred embodiments the cells are mammalian cells. In other preferred embodiments the cells are yeast cells, with cells from the genera *Saccharomyces* or *Schizosaccharomyces* being more preferred. The host cells can be derived from primary cells, or from transformed and/or immortalized cell lines.

The subject assays provide a means for detecting the ability of compounds to modulate the signal transduction activity of the target receptor by scoring for up- or down-regulation of a detection signal. Signal transduction can be measured in a variety of ways, including but not limited to, physical and biological methods, enzymatic methods, and transcriptional activation of endogenous genes or reporter genes. For example, endogenous yeast second messenger generation (e.g., GTP hydrolysis, calcium mobilization, or phospholipid hydrolysis) or increased transcription of an endogenous gene can be detected directly. Alternatively, the use of a reporter or indicator gene can provide a convenient readout. By whatever means measured, a change (e.g., a statistically significant change) in the detection signal can be used to facilitate isolation of compounds which modulate receptor or ion channel activities.

In one embodiment of the present invention, the test cells express the receptor of interest endogenously. In other embodiments, the test cells are engineered to express a heterologous receptor protein. In either of these embodiments, it may be desirable to inactivate one or more endogenous genes of the test and detector cells. For example, certain preferred embodiments in which a heterologous receptor is provided utilize test cells in which the gene for the homologous receptor has been inactivated. Likewise, other proteins involved in transducing signals from the target receptor can be inactivated, or complemented with an ortholog or paralog from another organism, e.g., yeast G protein subunits can be complemented by mammalian G protein subunits in yeast cells also engineered to express a mammalian G protein-coupled receptor. In this manner, a heterologous G protein-coupled receptor may be made to functionally couple with one or more endogenous signal transduction pathways in the cell. It is also possible to utilize a mutated endogenous or heterologous G protein subunit, or a chimera of native and heterologous G protein subunit molecules such that effective coupling of the G protein-coupled receptor to a signal transduction pathway is attained. Other complementations include, for example, expression of heterologous MAP kinases or erk kinases, MEKs or MKKs (MAP kinase kinases), MEKKs (MEK kinases), PAKs (p21-activated kinases, e.g., Ste20), ras and the like.

In one embodiment, the assay of the present invention can be used to screen compounds, e.g., small molecules, which are exogenously added to cells in order to identify potential receptor effector compounds. In another embodiment the subject assays enable rapid screening of large numbers of polypeptides in a library expressed in the cell in order to identify those polypeptides which agonize or antagonize receptor bioactivity, creating an autocrine system. The autocrine assay is characterized by the use of a library of recombinant test cells, each cell of which includes a target receptor protein whose signal transduction activity can be modulated by interaction with an extracellular signal, the transduction activity being able to generate a detectable signal, and an expressible recombinant gene encoding an exogenous test polypeptide from a polypeptide library. By the use of a gene library, the mixture of cells collectively expresses a population of test polypeptides. In preferred embodiments, the polypeptide library includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

In another embodiment, the assay of the present invention may be used to select for compounds having antagonistic activity to components of the pheromone pathway in yeast, or which are antagonistic to signaling coupled to the pheromone pathway. In this selection assay, the detector cell carries a construct which confers a growth phenotype coupled in such a manner as to respond inversely to activation of the signal pathway (i.e., the detector cell responds to alpha factor by reducing transcription of the detected gene product, or enzyme activity necessary for growth). This can be achieved, for instance, by regulating the detector gene by a tetracycline operator/repressor system (tet operator/tetR) and placing the tetracycline repressor under the control of the a factor response pathway of the detector cell and the detected gene is under tet regulation. Exposure of the detector cell to a factor then results in transcription of the tetR repressor which in turn reduces the transcription of the detector gene necessary for readout quantitation or for growth.

In this way, if the detector gene is controlled by a constitutive promoter but is repressed by tetR, the detector gene is not expressed. Such is the case when a factor is produced by the first cell with an activated pheromone response pathway (e.g., as a result of a functionally coupled GPCR by its cognate ligand or a small molecule agonist). When, however, an antagonist of the signaling component (the GPCR in the above example) is added, the signal is reduced or abrogated and the tetR transcription is decreased which releases the transcriptional repression of the detector gene which is transcriptionally activated. The more the tetR transcription is reduced, the greater the release of repression of the detector gene. This allows growth or increased expression of the gene product quantitated in the screen.

In another embodiment of the assay, if a test compound does not appear to directly induce the activity of the target receptor protein, the assay may be repeated and modified by the introduction of a step in which the test cell is first contacted with a known activator of the target receptor to induce the signal transduction pathways from the receptor. Thus, a test compound can be assayed for its ability to antagonize, e.g., inhibit or block the activity of the activator. Alternatively, the assay can score for test compounds which potentiate the induction response generated by treatment of the cell with a known activator. As set out above, the invention relates to methods for identifying compounds from among a set or collection or library of one or more compounds that modulate the activity of a signal transduction pathway in a cell. The pathway may be an endogenous signal transduction pathway within the cell (for example, the pheromone response pathway in a yeast cell), or may comprise one or more surrogate components which function in place of a natural component of the pathway.

Test compounds which act as agonists are detected as compounds which cause an increase in detectable signal as compared with the signal in the absence of the test compound. In another aspect, the effect of the test compounds on cells that are essentially identical except for the presence or absence of a target protein (e.g., a receptor, an ion channel, or a signal transduction pathway component surrogate) can be detected. Compounds which act as antagonists are detected as those which cause a decrease in the detectable signal generated by an agonist or a natural stimulator of signal transduction pathway when compared with the same cell in the absence of the test compound.

Alternatively, the target specificity of the test compound may be assessed by comparing the detectable signals generated in cells which differ only in the surrogate component of the signal transduction pathway. For example, cells which comprise different functionally coupled G protein-coupled receptors (GPCRs) may be compared in this way. Differences in detectable signal may then be ascribed to the GPCRs and may be distinguished from effects due to components present in each cell. In another embodiment, the cells may differ in that one cell comprises a functional surrogate signal transduction component (e.g., mammalian GPCR) whereas the other is identical except that the natural component is substituted for the functional surrogate.

By this method, compounds which induce a signal pathway from a particular receptor or channel can be identified. If a test compound does not appear to induce the activity of the receptor/channel protein, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

The method of the present invention is useful for identifying compounds that interact with any receptor protein whose activity ultimately induces a signal transduction cascade in the test cell which can be exploited to produce a detectable signal. In particular, the assays can be used to test functional ligand-receptor or ligand-ion channel interactions for cell surface-localized receptors and channels, and also for cytoplasmic and nuclear receptors. As described in more detail below, the subject assay can be used to identify effectors of, for example, G protein-coupled receptors, receptor tyrosine kinases, cytokine receptors, and ion channels, as well as steroid hormone, or other nuclear receptors. In certain embodiments the method described herein is used for identifying ligands for "orphan receptors" for which no ligand is known.

In embodiments utilizing an "autocrine cell" of the present invention, and in which cell surface receptors are the assay targets, it will be desirable for each of the peptides of the peptide library to include a signal sequence for secretion. In certain embodiments the expression of such a signal sequence may ensure appropriate transport of the peptide to the endoplasmic reticulum, the golgi, and ultimately to the cell surface. When a yeast cell is the test cell, in certain embodiments, the signal sequence will transport peptides to the periplasmic space, however, such transport may not be necessary to achieve autocrine stimulation.

Any transfectable cell that can express the desired cell surface protein in a manner such the protein finctions to transduce intracellularly an extracellular signal may be used as the test cell. Similarly, any cell surface protein that is known to those of skill in the art or that may be identified by those of skill in the art may used in the assay. The cell surface protein may be endogenously expressed on the selected cell or it may be expressed from cloned DNA.

In one embodiment of the invention, the detectable signal will be generated by an endogenous gene at its natural location in the genome of the detector cell. The endogenous gene is naturally responsive to the signal transduction pathway of interest in the detector cell, thereby providing "endogenous signaling".

In another embodiment of the invention, an indicator gene or "reporter gene" is inserted into the detector cell that will produce a detection signal upon activation of a signal transduction pathway of the detector cell. Typically, the indicator gene is in operative linkage with one or more transcriptional control elements, the activity of which is indirectly regulated by the signal transduction activity of the target receptor, with the level of expression of the indicator gene providing the receptor-dependent detection signal. The amount of transcription from the indicator gene may be measured using any method known to those of skill in the art to be suitable. In certain embodiments, indicator genes produce a spectrometrically active label, e.g., changes in color, fluorescence or luminescence, which can be readily measured by assays well known in the art.

Alternatively, the indicator gene can be a metabolic enzyme that relieves a cell's nutritional requirement, confers a growth signal, or provides resistance to a drug. For example, in one embodiment, the imidazoleglycerol phosphate dehydratase (IGP dehydratase) (i.e., the His3 enzyme) can be used as a re the cell is auxotrophic for histidine (requires histidine for growth) in the absence of activation. Activation of the His3 enzyme, under control of the signal transduction responsive transcriptional element, causes the cell to become prototrophic for histidine (does not require histidine). Thus the selection is for growth in the absence of histidine. Since only a few molecules per cell of IGP dehydratase are required for histidine prototrophy, the assay is very sensitive. The enzyme may also confer sensitivity to drugs for counterselection purposes, e.g., canavanine or cycloheximide.

Examples of indicator genes, including heterologous genes as well as endogenous yeast genes that are not normally responsive to the signal transduction pathway, suitable for use in accordance with the invention include, but are not limited to, ADE1, ADE2, ADE3, ADE4, ADE5, ADE7, ADE8, ASP3, ARG1, ARG3, ARG4, ARG5, ARG6, ARG8, ARO2, ARO7, BAR1, CAT, CHO1, CYS3, GAL1, GAL7, GAL10, GFP, HIS1, HIS3, HIS4, HIS5, HOM3, HOM6, ILV1, ILV2, ILV5, INO1, INO2, INO4, lacZ LEU1, LEU2, LEU4, luciferase, LYS2, MAL, MEL MET2, MET3, MET4, MET8, MET9, MET14, MET16, MET19, OLE1, PHO5, PRO1, PRO3, THR1, THR4, TRP1, TRP2, TRP3, TRP4, TRP5, URA1, URA2, URA3, URA4, URA5 and URA10. Preferred indicator genes include CAT, GAL1, GAL7, GAL10, GFP, HIS3, lacZ, luciferase, LEU2, MEL, PHO5, Cdc25, Cyr1, Ras, and URA3.

Transcriptional control elements for operative linking to an indicator gene, or for modifying the genomic locus of an indicator gene include, include but are not limited to, promoters, enhancers, and operators, the activities of which are responsive to cellular signal transduction pathways. An example of such a transcriptional control element is the FUS1 promoter which is activated by signal transduction through the pheromone response pathway (U.S. Pat. No. 5,063,154 to Fink et al).

III. Host Cells

Suitable cells for generating the subject assay include prokaryotes, yeast, or higher eukaryotic cells, including plant and animal cells, especially mammalian cells. Prokaryotes include gram negative or gram positive organisms. Examples of suitable mammalian host cell lines include the COS-7 line of monkey kidney cells (ATCC CRL 1651) (Gluzman (1981) Cell 23:175) CV-1 cells (ATCC CCL 70), L cells, C127, 3T3, Chinese hamster ovary (CHO), HeLa, HEK-293, SWISS 3T3, and BHK cell lines.

If yeast cells are used, the yeast may be of any species which are cultivable and in which an exogenous receptor can be made to engage the appropriate signal transduction machinery of the host cell. Suitable species include *Kluyveromyces lactis, Schizosaccharomyces pombe*, and *Ustilago maydis; Saccharomyces cerevisiae* is preferred. In a preferred embodiment of the assay, the test yeast cell is of the opposite mating type to that of the detector yeast cell, with a MATα test cell and a MATa detector cell being particularly preferred.

Other yeast which can be used in practicing the present invention are *Neurospora crassa, Aspergillus niger, Aspergillus nidulans, Pichiapastoris, Candida tropicalis*, and *Hansenula polymorpha*. The term "yeast", as used herein, includes not only yeast in a strictly taxonomic sense, i.e., unicellular organisms, but also yeast-like multicellular fungi or filamentous fungi.

It will be understood that to achieve selection or screening, the detector cell must have an appropriate phenotype. For example, generating a pheromone-responsive chimeric HIS3 gene in a yeast that has a wild-type HIS3 gene would frustrate genetic selection. Thus, to achieve nutritional selection, an auxotrophic strain is preferred.

A variety of complementations for use in the subject assay can be constructed. Indeed, many yeast genetic complementations with mammalian signal transduction proteins have been described in the art. For example, Mosteller et al. (1994) *Mol. Cell Biol.* 14:1104–12 demonstrates that human Ras proteins can complement loss of ras mutations in *S. cerevisiae*. Moreover, Toda et al. (1986) *Princess Takamatsu Symp* 17: 253–60 have shown that human Ras proteins can complement the loss of Ras1 and Ras2 proteins in yeast, and hence are functionally homologous. Both human and yeast Ras proteins can stimulate the magnesium and guanine nucleotide-dependent adenylate cyclase activity present in yeast membranes. Ballester et al. (1989) *Cell* 59: 681–6 describe a vector to express the mammalian GAP protein in the yeast *S. cerevisiae*. When expressed in yeast, GAP inhibits the function of the human Ras protein, and complements the loss of IRA1. IRA1 is a yeast gene that encodes a protein with homology to GAP and acts upstream of Ras. Mammalian GAP can therefore function in yeast and interact with Ras yeast. Wei et al. (1994) *Gene* 151: 279–84 describes that a human Ras-specific guanine nucleotide-exchange factor, Cdc25GEF, can complement the loss of Cdc25 function in *S. cerevisiae*. Martegani et al. (1992) *EMBO J* 11: 2151–7 describe the cloning by functional complementation of a mouse cDNA encoding a homologue of Cdc25, a *Saccharomyces cerevisiae* Ras activator. Vojtek et al. (1993) *J. Cell Sci.* 105: 777–85 and Matviw et al. (1992) *Mol. Cell Biol.* 12: 5033–40 describe how a mouse CAP protein, e.g., an adenylyl cyclase associated protein associated with Ras-mediated signal transduction, can complement defects in *S. cerevisiae*. Papasavvas et al. (1992) *Biochem. Biophys. Res. Commun.* 184:1378–85 also suggest that inactivated yeast adenylyl cyclase can be complemented by a mammalian adenylyl cyclase gene. Hughes et al. (1993) *Nature* 364: 349–52 describe the complementation of byr1 in fission yeast by mammalian MAP kinase (MEK). Parissenti et al. (1993) *Mol Cell Endocrinol* 98: 9–16 describe the reconstitution of bovine protein kinase C (PKC) in yeast. The $Ca^{2+}$ and phospholipid-dependent Ser/Thr kinase PKC plays important roles in the transduction of cellular signals in mammalian cells. Marcus et al. (1995) *P.N.A.S.* 92: 6180–4 suggest the complementation of shk1 null mutations in *S. pombe* by either the structurally related *S. cerevisiae* Ste20 or mammalian p65PAK protein kinases.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of an inactivated gene of the host cell is supplied by an exogenous nucleic acid. For instance, yeast cells can be "mammalianized", and even "humanized", by complementation of receptor and signal transduction proteins with mammalian homologs. To illustrate, inactivation of a yeast Byr2/Ste1 1 gene can be complemented by expression of a human MEKK gene.

In certain embodiments (particularly those in which an autocrine peptide library is employed), the growth arrest consequent to activation of the pheromone response pathway is an undesirable effect since cells that bind agonists stop growing while surrounding cells that fail to bind peptides will continue to grow. The cells of interest, then, will be overgrown or their detection obscured by the background cells, confounding identification of the compound of interest. To overcome this problem the present invention teaches engineering the cell such that: 1) growth arrest does not occur as a result of exogenous signal pathway activation (e.g., by inactivation of the FAR1gene); and/or 2) a selective growth advantage is conferred by activating the pathway.

It is desirable that the exogenous receptor be exposed on a continuing basis to the test compound. Unfortunately, this is likely to result in desensitization of the pheromone response pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) *Mol. Cell. Biol.* 13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations, e.g., STE50, SGV1, BAR1, STE2, STE3, PIK1, MSG5, SIG1and AFT1, have the similar effect of increasing the sensitivity of the bioassay. Thus desensitization may be avoided by mutating (which may include deleting) the SST2 gene so that it no longer produces a functional protein, or by mutating one of the other genes listed above.

IV. Expression Systems

Ligating a polynucleotide coding sequence into a gene construct, such as an expression vector, and transforming or transfecting into hosts, either eukaryotic (yeast, avian, insect or mammalian) or prokaryotic (bacterial cells), are standard procedures used in producing other well-known proteins, including sequences encoding exogenous receptor and peptide libraries. Similar procedures, or modifications thereof, can be employed to prepare recombinant reagent cells of the present invention by tissue-culture technology in accord with the subject invention.

In general, it will be desirable that the vector be capable of replication in the host cell. It may be DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (Cloning Vectors: A Laboratory Manual, Elsevier, New York, 1985). Mammalian expression vectors may comprise non-transcribed elements such as an origin of replication, a suitable promoter and enhancer linked to the gene to be expressed, other 5' or 3' flanking nontranscribed sequences, 5' or 3' nontranslated sequences, such as necessary ribosome binding sites, a poly-adenylation site, splice donor and acceptor sites, and transcriptional termination sequences.

Preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

Transcriptional and translational control sequences in expression vectors to be used in transforming mammalian cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al.(1978) *Nature* 273:11 1). Smaller or larger SV40 fragments may also be used, provided the approximately 250 bp sequence extending from the Hind III site toward the Bgl I site located in the viral origin of replication is included. Exemplary vectors can be constructed as disclosed by Okayama and Berg (1983, *Mol Cell Biol* 3:280). A useful system for stable high level expression of mammalian receptor cDNAs in C127 murine mammary epithelial cells can be constructed substantially as described by Cosman et al. (1986, *Mol. Immunol.* 23:935). Other expression vectors for use in mammalian host cells are derived from retroviruses.

In other embodiments, the use of viral transfection can provide stably integrated copies of the expression construct. In particular, the use of retroviral, adenoviral or adeno-associated viral vectors is contemplated as a means for providing a stably transfected cell line which expresses an exogenous receptor, and/or a polypeptide library.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae*due to the replication determinant of the yeast 2 micron plasmid. In addition, drug resistance markers such as ampicillin can be used. Moreover, if yeast are used as a host cell, it will be understood that the expression of a gene in a yeast cell requires a promoter which is functional in yeast Suitable promoters include the promoters for metallothionein, 3-phosphoglycerate kinase (Hitzeman et al., *J. Biol. Chem.* 255, 2073 1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose, galactose and melibiose utilization. Finally, promoters that are active in only one of the two haploid mating types may be appropriate in certain circumstances. Among these haploid-specific promoters, the pheromone promoters MFa1 and MFα1 are of particular interest.

In some instances, it may be desirable to use insect cells as the host cells. In such embodiments, recombinant polypeptides can be expressed by the use of a baculovirus expression system. Examples of such baculovirus expression systems include pVL-derived vectors (such as pVL1392, pVL1393 and pVL941), pAcUW1-derived vectors (such as pAcUW1), and pBlueBac-derived vectors (such as the β-gal containing pBlueBac III).

In constructing suitable expression plasmids, the termination sequences associated with these genes, or with other genes which are efficiently expressed in yeast, may also be ligated into the expression vector 3' of the heterologous coding sequences to provide polyadenylation and termination of the mRNA.

V. Receptors

Receptor proteins (e.g., pheromone system protein surrogates) for use in the present invention can be any receptor or ion channel which interacts with an extracellular molecule (i.e., hormone, growth factor, peptide, ion) to modulate a signal in the cell. To illustrate, the receptor can be a cell surface receptor or, in other embodiments, an intracellular receptor. In certain embodiments, the receptor is a cell surface receptor, such as: a receptor tyrosine kinase, e.g., an EPH receptor; an ion channel; a cytokine receptor; a chemokine receptor; a growth factor receptor; or a G protein-coupled receptor, such as a chemoattractant peptide receptor, a neuropeptide receptor, a light receptor, a neurotransmitter receptor, or a polypeptide hormone receptor. In a preferred embodiment, the pheromone system protein surrogate to be assayed is selected from the group consisting of G protein-coupled receptors, G proteins, proteases, kinases, farnesyl transferases, carboxymethyl transferases, ABC transporters and cyclins. In addition, the subject assay can be used to identify ligands for an orphan receptor, i e., a receptor with no known ligand, regardless of the class of receptors to which it belongs.

In those embodiments wherein the target receptor is a cell surface receptor and the cell expresses a peptide library, it may be desirable, in certain embodiments, for the peptides in the library to express a signal sequence to ensure that the peptides are processed in the appropriate secretory pathway and thus are available to interact with receptors on the cell surface.

G Protein-Coupled Receptors

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha (α), beta (β) and gamma (γ) subunits, are complexed with the nucleotide guanosine diphosphate (GDP) and are in contact with receptors. When a hormone or other first messenger binds to a receptor, the receptor changes conformation and this alters its interaction with the G protein. This spurs the a subunit to release GDP, and the more abundant nucleotide guanosine triphosphate (GTP), replaces it, activating the G protein. The G protein then dissociates to separate the α subunit from the still complexed beta and gamma subunits. Either the Gα subunit, or the Gβγ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the Gα converts the GTP to GDP, thereby inactivating itself. The inactivated Gα may then reassociate with the Gβγ complex.

Hundreds, if not thousands, of receptors convey messages through heterotrimeric G proteins, of which at least 17 distinct forms have been isolated. Although the greatest variability has been seen in the α subunit, several different β and γ structures have been reported. There are, additionally, many different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) *Cell* 72, 415; Kouba et al. *FEBS Lett.* (1993)321, 173; and Birkenbach et al. (1993) *J. Virol.* 67,2209.

The "exogenous receptors" of the present invention may be any G protein-coupled receptor, preferably exogenous to the cell, which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein-coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, histamine, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (1 h/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Preferred G protein-coupled receptors include, but are not limited to: α1A-adrenergic receptor, α1B-adrenergic receptor, α2-adrenergic receptor, α2B-adrenergic receptor, β1-adrenergic receptor, β2-adrenergic receptor, β3-adrenergic receptor, ml acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2a adenosine receptor, A2b adenosine receptor, A3 adenosine receptor, 5-HTl1a receptor, 5-HT1b receptor, 5HT1-like receptor, 5-HT1d receptor, 5HT1d-like receptor, 5HT1d beta receptor, substance K (neurokinin A) receptor, fMLP receptor (FPR), fMLP-like receptor (FPRL-1), angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, CXCR1(IL-8 receptor A), CXCR2 (IL-8 receptor B), Delta Opioid receptor, Kappa Opioid receptor, mip-1alpha/RANTES receptor (CRR1), Rhodopsin, Red opsin, Green opsin, Blue opsin, metabotropic glutamate mGluR1–6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor. In addition, there are at least five receptors (CC and CXC receptors) involved in HIV viral attachment to cells. The two major co-receptors for HIV are CXCR4, (fusin receptor, LESTR, SDF1 receptor) and CCR5 (m-trophic). More preferred receptors include the following human receptors: melatonin receptor 1a, galanin receptor 1, neurotensin receptor, adenosine receptor 2a, somatostatin receptor 2 and corticotropin releasing factor receptor 1. Melatonin receptor 1a is particularly preferred. Other G protein-coupled receptors (GPCRs) are known in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include STE2, STE3, Gal1, and Gal10. Suitable signal sequences include those of STE2, STE3 and of other genes which encode proteins secreted by yeast cells. Preferably, when a yeast cell is used, the codons of the gene would be optimized for expression in yeast. See Hoekema et al., (1987) *Mol. Cell. Biol.*, 7:2914–24; Sharp, et al., (1986)14:5125–43.

The homology of STRs is discussed in Dohlman et al., *Ann. Rev. Biochem.*, (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

In certain embodiments, the endogenous yeast G protein will be sufficiently homologous to the cognate G protein which is natively associated with the wild-type exogenous G protein-coupled receptor for coupling to occur such that the receptor will be functional. For example, the human somatostatin receptor will functionally couple to the endogenous yeast GPA-1 subunit.

In other embodiments, the wild-type exogenous G protein-coupled receptor cannot be made functional in yeast, but may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible. For example, the V-VI loop of a heterologous G protein-coupled receptor could be replaced with that of the yeast STE2 or STE3 receptor).

In yet another embodiment, a compatible G protein can be provided. A compatible G protein for use in the instant assays can include a heterologous or chimeric G protein subunit (or subunits) such as those described in the art (see e.g., PCT PCT/US94/03143). Preferably, the yeast genome is modified so that it is unable to produce the yeast receptors which are homologous to the exogenous receptors in functional form.

VII. Test Compounds

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

If a test compound fails to stimulate the activity of a receptor, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

A. Exogenously Added Compounds

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al 1992. *J. Am. Chem. Soc.* 114:10987; DeWitt et al. peptoids (Zuckermann. 1994. *J. Med. Chem.* 37:2678) oligocarbamates (Cho et al. 1993. *Science* 261:1303), and hydantoins (DeWitt et al. supra). Rebek et al. have described an approach for the synthesis of molecular libraries of small organic molecules with a diversity of 104–105 (Carell et al. 1994. *Angew. Chem. Int. Ed. Engl.* 33:2059; Carell et al. *Angew. Chem. Int. Ed. Engl.* 1994.33:2061).

The compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. *Anticancer Drug Des.* 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. *Proc. Natl. Acad. Sci.* USA 91:11422; Horwell et al. 1996 *Immunopharmacology* 33:68; and in Gallop et al. 1994. *J. Med. Chem.* 37:1233. In addition, libraries such as those described in the commonly owned applications U.S. Ser. No. 08/864,241, U.S. Ser. No. 08/864,240 and U.S. Ser. No. 08/835,623 can be used to provide compounds for testing in the present invention.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc. Natl. Acad. Sci.* USA 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; and Ladner, supra).

Other types of peptide libraries may also be expressed, see, e.g., U.S. Pat. Nos. 5,270,181 and 5,292,646; and PCT publication WO94/02502). In still another embodiment, the combinatorial polypeptides are produced from a cDNA library.

B. Peptide Libraries

In certain embodiments, yeast cells can be engineered to produce the compounds to be tested. This assay system has the advantage of increasing the effective concentration of the compound to be tested. In one embodiment, a method such as that described in WO 94/23025 can be utilized.

Other methods can also be used. As mentioned above, peptide libraries are systems which simultaneously display, in a form which permits interaction with a target, a highly diverse and numerous collection of peptides. Many of the systems known in the art for presentation of peptides in a library are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. Although a cell surface receptor may be used as a target, the screening will not reveal whether the binding of the peptide caused an allosteric change in the conformation of the receptor.

The Ladner et al. patent, U.S. Pat. No. 5,096,815, describes a method of identifying novel proteins or polypeptides with a desired DNA binding activity. Semi-random ("variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol. Chem.* (1989) 264, 20206 and Kaiser et al. (1987) *Science* 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/02502). The combinatorial peptide can be attached to one of the termini of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is derived to express a combinatorial library of polypeptides which are based at least in part on a known polypeptide sequence or a portion thereof (not a cDNA library). That is, the sequences of the library are semi-random, being derived by combinatorial mutagenesis of a known sequence. (See, e.g., Ladner et al. PCT publication WO 90/02909; Garrard et al., PCT publication WO 92/09690; Marks et al. (1992) *J. Biol. Chem.* 267:16007–16010; Griffths et al. (1993) *E.M.B.O. J* 12:725–734; Clackson et al. (1991) *Nature* 352:624–628; and Barbas e are known ligands for a target receptor can be mutagenized by standard techniques to derive a variegated library of polypeptide sequences which can further be screened for agonists and/or antagonists. This library can be expressed in a reagent cell of the present invention, and other receptor activators can be isolated from the library. This has permitted the identification of even more potent FPRL-1 surrogate ligands (Klein et al., supra).

Alternatively, the library can be expressed under conditions wherein the cells are in contact with the original tridecapeptide, e.g., the FPRL-1 receptor is being induced by that surrogate ligand. Peptides from an expressed library can be isolated based on their ability to potentiate the induction, or to inhibit the induction, caused by the surrogate ligand. The latter of course will identify potential antagonists of chemoattractant receptors. In still other embodiments, the surrogate ligand can be used to screen exogenous compound libraries (peptide and non-peptide) which, by modulating the activity of the identified surrogate, will presumably also similarly effect the native ligand's effect on the target receptor. In such embodiments, the surrogate ligand can be applied to the cells, though is preferably produced by the reagent cell, thereby providing an autocrine cell.

In still another embodiment, the combinatorial polypeptides are produced from a cDNA library.

In a preferred embodiment of the present invention, the yeast cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

C Periplasmic Secretion

In those embodiments of the invention in which yeast cells are used as the host cell and the compounds tested are endogenously expressed from a library, it will be noted that the yeast cell is bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Because this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the α-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

Exemplification

The invention will be more readily understood by reference to the following examples, which are included merely for purposes of illustration of certain aspects and embodiments of the present invention and are not intended to limit the invention.

Materials and Methods

The yeast strains and plasmids used in the following examples are set forth in Table 1.

TABLE 1

Strains and plasmids

Strains

| STRAIN ID | ALIAS | MATING TYPE | GENOTYPE |
| --- | --- | --- | --- |
| CY13858 | CY10981/2695 | α | FUS1p-HIS3 GPA1-3907 can1 far1*1442 his3 leu2 lys2 sst2*2 ste14::trp1::LYS2 ste3*1156 tbt1-1 trp1 ura3 |
| CY10981 | CY2120-GPA1-1 | α | FUS1p-HIS3 GPA1-3907 can1 far1*1442his3 leu2 lys2 sst2*2 ste14::trp1::LYS2 ste3*1156 tbt1-1 trp1 ura3 |
| BOY843 | W303-1A bar1::LEU2 | a | bar1::LEU2 ade2-1 can1–100 his3–11, 15 leu2–3, 112 trp1-1 ura3-1 |
| CY17911 | CY10103/Mfα1del-B | α | FUS1p-HIS3 STE18g6-3841 ade2*3447 ade8*3457 can1 cyh2 far1*1442 gpa1(41)-G α i2 his3 leu2 lys2 mf α 1*loxP-KanR-loxP ste14::trp1::LYS2 ste3*1156 tbt1-1 trp1 ura3 |
| CY18592 | CY10981/mfα1*6180 #3 | α | FUS1p-HIS3 GPA1-3907 can1 far1*1442 his3 leu2 lys2 mf α 1*6180 sst2*2 ste14::trp1::LYS2 ste3*1156 tbt1-1 trp1 ura3 |
| CY18594 | CY10981/mfα1*6180 #3/CP1289 | α | FUS1p-HIS3 GPA1-3907 can1 far1*1442 his3 leu2 lys2 mf α 1*6180 sst2*2 ste14::trp1::LYS2 ste3*1156 tbt1-1 trp1 ura3 |
| CY18596 | CY10981/mfα1*6180 #3 CP2695 | α | FUS1p-HIS3 GPA1-3907 can1 far1*1442 his3 leu2 lys2 mf α 1*6180 sst2*2 ste14::trp1::LYS2 ste3*1156 tbt1-1 trp1 ura3 |
| CY18632 | CY13397/6180 | α | FUS1p-HIS3 GPA1G α q(5) can1 far1*1442 his3 leu2 lys2 mf α 1*6180 sst2*2 ste14::trp1::LYS2 ste18g6-3841 ste3*1156 tbt1-1 trp1 ura3 |
| CY18634 | CY13399/6180 | α | FUS1p-HIS3 GPA1G α s(5) can1 far1*1442 his3 leu2 lys2 mf@1*6180 sst2*2 ste14::trp1::LYS2 ste18g6-3841 ste3*1156 tbt1-1 trp1 ura3 |
| CY18636 | CY11063/6180 | α | FUS1p-HIS3 GPA1p-G α sE10k can1 far1*1442 his3 leu2 lys2 mf@1*6180 ste14::trp1::LYS2 ste18g6-3841 ste3*1156 tbt1-1 trp1 ura3 |
| CY18908 | CY18190/mf α 1 del A | α | FUS1p-HIS3 GPA1G α z(5) STE18g6-3841 can1 far1*1442 his3 kre1::hisG leu2 lys2 mf α 1*6180 sst2*2 ste14::trp1::LYS2 ste3*1156 tbt1-1 trp1 ura3 |
| CY18782 | CY8342/mfα1 delete | α | FUS1p-HIS3 can1 far1*1442 gpa1p-rG α sE10K his3 leu2 lys2 mf α 1*6180 ste14::trp1::LYS2 ste3*1156 tbt1-1 trp1 ura3 |
| CY18778 | CY12950/mfα1 delete | α | FUS1p-HIS3 GPA1-G α q(5) can1 far1*1442 his3 leu2 lys2 mf α 1*6180 sst2*2 ste14::trp1::LYS2 ste3*1156 tbt1-1 trp1 ura3 |
| CY18876 | CY17010/mfα1 del B | α | FUS1p-HIS3 G α q(1–21)-GPA1(24–467)-G α q(5) STE18g6-3841 can1 far1*1442 his3 leu2 lys2 mf α 1*6180 sst2*2 ste14::trp1::LYS2 ste3*1156 tbt1-1 trp1 ura3 |
| CY18879 | CY17020/mfα1 del A | α | FUS1p-HIS3 G α q(1–21)-GPA1(24–467)-G α q(5) can1 far1*1442 his3 leu2 lys2 mf α 1*6180 sst2*2 ste14::trp1::LYS2 ste3*1156 tbt1-1 trp1 ura3 |

TABLE 1-continued

Strains and plasmids

Plasmids

| CLONE ID | INSERT | MARKER |
|---|---|---|
| CP5513 | NPY-Y1 | 2mu-ori AmpR LEU2 PGKp-MFα1leaderKREAEA-NPY-Y1-PHO5term REP3 |
| CP5517 | NPY-Y2 | 2mu-ori AmpR LEU2 PGKp-MFα1leaderKREAEA-NPY-Y2-PHO5term REP3 |
| CP5396 | human CRF1 receptor | LEU2 PGKp-2mu-ori-REP3-AmpR-hCRF1_receptor |
| CP5095 | Human adenosine 1 receptor | 2mu-ori AmpR LEU2 PGKp-MFα1leader-hA1R-PHO5term REP3 |
| CP4110 | rat VIP-1 PCRed from plasmid 4107 | 2mu-ori AmpR LEU2 PGKp-rVIP-1 REP3 |
| CP3776 | Human Somatostatin Receptor (HSSTR2) | LEU2 PGKp-2mu-ori-REP3-AmpR-human_Somatostatin_receptor_(SSTR2) |
| CP1930 | human BK2R | 2mu-ori AmpR LEU2 PGKp-BK2R REP3 |
| CP1766 | | 2mu-ori AmpR LEU2 PGKp-A2aR REP3 |
| CP1304 | | 2mu-ori AmpR LEU2 PGKp-PAFR REP3 |
| CP1212 | | 2mu-ori AmpR FUS1-LacZ REP3 URA3 |
| CP2695 | | 2mu-ori AmpR LEU2 PGKp-ML1aR REP3 |
| CP6180 | MFα1del | AmpR MF α 1del URA3 |
| CP4259 | Human neurotensin receptor | 2mu-ori AmpR LEU2 PGKp-MFα1leader-hNTR-PHO5term REP3 |
| CP6161 | SDF-1α with an N-terminal extension of DG. | 2mu-ori ADHp-prepro α F-KREAEADG-SDF-1 α AmpR REP3 URA3 f1-ori |
| CP6281 | Human adenosine 2b receptor | 2mu-ori AmpR LEU2 PGKp-hA2bR REP3 |
| CP1289 | | 2mu-ori AmpR LEU2 PGKp REP3 |
| CP6416 | sheep GHSR | 2mu-ori AmpR LEU2 PGKp-MFα1prepro-sGHSR-FLU-PHO5t REP3 |
| CP3693 | PCR product encoding human ML1b receptor | 2mu-ori AmpR LEU2 PGKp-ML1bR REP3 |
| CP6073 | Y5/Y1 chimera PCR product | 2mu-ori AmpR LEU2 PGKp-MFα1leaderKREAEA-NPY-Y5-Y1(IL3)-Y5-PHO5t REP3 |

EXAMPLE 1

Detection of Ligand Activation of Pheromone Response Pathway Using Two Cell Assay System This example demonstrates the utility of the assay system of the present invention for the detection of the activity of the mating factor response pathway in response to activation of a pathway-coupled receptor by its cognate ligand. Similarly, this system can be used to determine the agonist or antagonist activity of a test compound for a given receptor coupled to the aforementioned pathway, and also to identify ligands for orphan receptors coupled to this pathway.

As depicted in FIG. 1, the assay system comprises a first, test MATα S. cerevisiae yeast cell having a heterologous G protein-coupled receptor functionally coupled to the pheromone response pathway and a second, detector MATa S. cerevisiae yeast cell having a lacZ reporter gene fused to the FUS1 promoter. Binding of cognate ligand to the heterologous receptor in the test cell activates the receptor, causing a signal to be transduced through the pheromone response pathway, ultimately resulting in the secretion of α-factor from the cell. Specific receptors at the surface of the detector cells bind to the secreted α-factor and are activated by it, resulting in the transduction of a signal through the pheromone response pathway in these cells, and activating the transcription of the lacZ gene. The activity of the β-galactosidase expressed from this lacZ gene may be determined and thereby enables a determination of the activity of the pheromone response pathway in the first, test cells.

A strain of test cells was established by transforming (transfecting) a culture of S. cerevisiae yeast cells with the human1a (ML1a) receptor gene. Cultures of MATα test cells containing a heterologous ML1a receptor (CY1 3858) and MATa detector cells (a CY19 related strain containing the CP1212 FUS1p-LacZ plasmid) were grown overnight to stationary phase in media selective for the maintenance of the plasmids (SCD-leu media for the MATα cells and SCD-ura for the MATa cells). The cells were diluted with additional medium and permitted to recover from stationary phase for several hours. After determination of the optical density of the cultures, the cells were harvested by centrifugation, were washed once in non-selective synthetic medium, and were resuspended in non-selective medium at an approximate optical density (measured at 600 nm) of 0.4. MATα and MATa cells were then transferred to a 96-well plate and an appropriate ligand (α-factor at a final concentration of 1–5 micromolar or melatonin at a final concentration of 5 micromolar) was added to the assay system. The final volume of cells, culture medium and ligand was about 100 microliters. The cells were mixed using a plate-mixer and incubated at 30° C. After 3 to 4 hours of incubation, β-galactosidase enzyme activity was determined as follows: 20 microliters of a mix of Triton (2.5%) and chlorophenol red-β-D-galactopyranoside (CPRG) (6 mg/ml) in 6× Z-buffer was added, and the plates were incubated at 37° C. until a clear change in color from yellow to red could be observed. The reaction was then stopped by the addition of 60 microliters 1 M sodium carbonate, and the absorbance at a wavelength of 575 nm was determined using a plate reader.

The results are depicted in Table 2. In the absence of an appropriate ligand for the ML1 a receptor (leftmost column) there is a response corresponding to approximately 1.1 units of β-galactosidase activity in the detector cells, while in the presence of melatonin, there is an increase in detected β-galactosidase activity, to approximately 1.8 units. This approximately 1.6-fold induction in activity is both statistically significant and reproducible. In all cases, virtually no β-galactosidase

TABLE 3

Transcriptional induction of various mating factor genes

|  |  | # of repeats | Mating factor production | Ref. | mRNA -fold induction | Ref. |
|---|---|---|---|---|---|---|
| MATa | MFa1 | 4 | 50% | [1] | 5x | [3] |
|  | MFa2 | 4 | 50% | [1] | 4x | [3] |
| MATα | MFα1 | 4 | 95% | [2] | 2–3x | [4] |
|  | MFα2 | 2 | 5% | [2] | 6x | [5] |

[1] Michaelis & Herskowitz (1988) Mol. Cell. Biol. 8: 309
[2] Kurjan (1985) Mol. Cell. Biol. 5: 787
[3] Spellman (1998) Mol. Cell. Biol. 9: 4507
[4] Achstetter (1989) Mol. Cell. Biol. 9: 4507
[5] Jarvis et al. (1988) Mol. Cell. Biol. 8: 309

Using the experimental protocol outlined in Example 1, MATα cells containing a plasmid encoding the ML1 a receptor, with and without the MFα1 gene (CY13858 and CY18596) were mixed with an equal number of MATa detector cells (with a FUS1p-LacZplasmid). After incubation for several hours at 30° C., β-galactosidase enzyme activity in the detector c As illustrated in Table 4, deletion of the MFα1 gene in the test cells resulted in a strong reduction in constitutive α-factor production, as detected by the MATα detector cells. Without the deletion, β-galactosidase activity is approximately 3.9 units in this experiment, while the presence of the deletion causes this value to drop to approximately 0.4 units of activity. Thus, the bulk of the constitutive expression and secretion of α-factor appears to have been eliminated by the inclusion of a MFα1 deletion in the test cells of this assay system.

TABLE 4

Constitutive production of α-factor from unstimulated MATα test cells both with and without deletion of the MFα1 gene, as detected by MATa detector cells.

|  | A575 no ligand |
|---|---|
| Test cells + detector cells | 3.9 –/+ 0.03 |
| Test cells lacking MFα1 gene + detector cells | 0.43 –/+ 0.02 |

Values in Table 4 represent the average and standard deviation of three replicate samples.

activity was observed in detector cells isolated from test cells, unless these detector cells were directly stimulated with α-factor.

TABLE 2

Induction of α-factor production in MATα test cells containing the melatonin ML1a receptor challenged with melatonin, as detected by MATa detector cells

|  | A575 no ligand | A575 +melatonin | A575 +α-mating factor |
|---|---|---|---|
| Detector cells only | 0.07 –/+ 0.01 | 0.07 –/+ 0.01 | 3.13 –/+ 0.07 |
| Test cells + Detector cells | 1.09 –/+ 0.18 | 1.77 –/+ 0.21 | 3.32 –/+ 0.07 |

Values in Table 2 represent the average and standard deviation of three replicate samples.

EXAMPLE 2

Deletion of the MFα1 Gene in Receptor Cells

One of the results of Example 1 was the finding that MATα ML1a-expressing test cells not stimulated with melatonin (and thereby not activating the pheromone response pathway) still secreted a considerable amount of α-factor. This constitutive expression and secretion of α-factor is disadvantageous, because weakly activating cognate ligands of the receptor in the detector cell may not stimulate a significant enough release of α-factor to be detectable over constitutive α-factor production. Data available in the literature suggest that the MFα1 and MFα2 genes are transcriptionally induced to different degrees (see Table 3) by stimulation of an a mating type cell with a-factor. Thus, experiments in which one of the two α-factor genes (MFα1) was deleted were undertaken in an attempt to lessen this background α-factor expression.

The percentages of contribution of each of the two mating factor genes to overall mating factor production are approximate and not mentioned as such in the references. Based on the fact that MFα2 is the more upregulated of the two upon a-factor stimulation, deletions of the MFα1 gene were made.

EXAMPLE 3

Induction of Mating Factor Production in MATα Receptor Cells Deleted for the MFα1 Gene One concern in deleting the MFα1 gene is that insufficient α-factor will be produced from the test cells upon activation of the G protein-coupled receptor to permit reasonable stimulation of FUS1-LacZ transcription in the detector cells. Thus, experiments were undertaken to assess the induction of mating factor production in test cells deleted for the MFα1 gene.

Using the experimental protocol described in Example 1, MATα test cells lacking the MFα1 gene and containing a plasmid encoding the ML1a receptor (CY18596) or a mock control plasmid (CY18594) were mixed with an equal number of MATa detector cells having a FUS1-LacZ plasmid. After incubation for several hours at 30° C. in the presence or absence of a ligand, either melatonin or exogenously added α-factor, the β-galactosidase enzyme activity was determined in the MATα detector cells.

As shown in Table 5, in the absence of ligand, approximately 0.4 units of β-galactosidase activity were observed in the MATa detector cells, regardless of the presence of the melatonin receptor in the MATα test cells. In the presence of the ligand melatonin, however, MATα test cells lacking the ML1 a receptor did not secrete any additional α-factor, while those expressing the ML1a receptor give rise to a large increase in α-factor production, as detected by the MATa detector cells. These cells demonstrated approximately 2.1 units of β-galactosidase activity, roughly a 5.2-fold increase in activity corresponding to the activation of the ML1a receptor by its cognate ligand, melatonin. This level of β-galactosidase activity is of the same magnitude as that produced when the detector cells are directly stimulated with exogenously added α-factor.

TABLE 5

Induction of α-factor production from test MATα cells deleted for the MFα1 gene and expressing the ML1a melatonin receptor upon challenge with melatonin, as detected by MATa detector cells.

|  | no ligand A575 | +melatonin A575 | fold induction | +α-mating factor A575 | fold induction |
|---|---|---|---|---|---|
| Test cells + mock plasmid | 0.35 −/+ 0.02 | 0.32 −/+ 0.01 | 0.9 | 2.48 −/+ 0.43 | 7.1 |
| Test cells + ML1a receptor | 0.43 −/+ 0.05 | 2.29 −/+ 0.38 | 5.3 | 2.10 −/+ 0.36 | 4.8 |

Values in Table 5 represent the average and standard deviation of three replicate samples

EXAMPLE 4

Dose-Response Curve for Induction of α-Factor Production in MATα Receptor Cells Deleted for the MFα1 Gene To assess the degree of sensitivity of the detector cells to changes in concentration of the ligand specific for a receptor in the test cell, experiments were performed in which MATα test cells deleted for the MFα1 gene and containing a plasmid encoding the ML1a receptor (CY18596) were mixed with an equal number of MATa detector cells having a FUS1p-LacZ plasmid. After incubation for several hours at 30° C. in the presence of various known concentrations of melatonin, β-galactosidase enzyme activity in the detector cells was determined.

Figure 2:
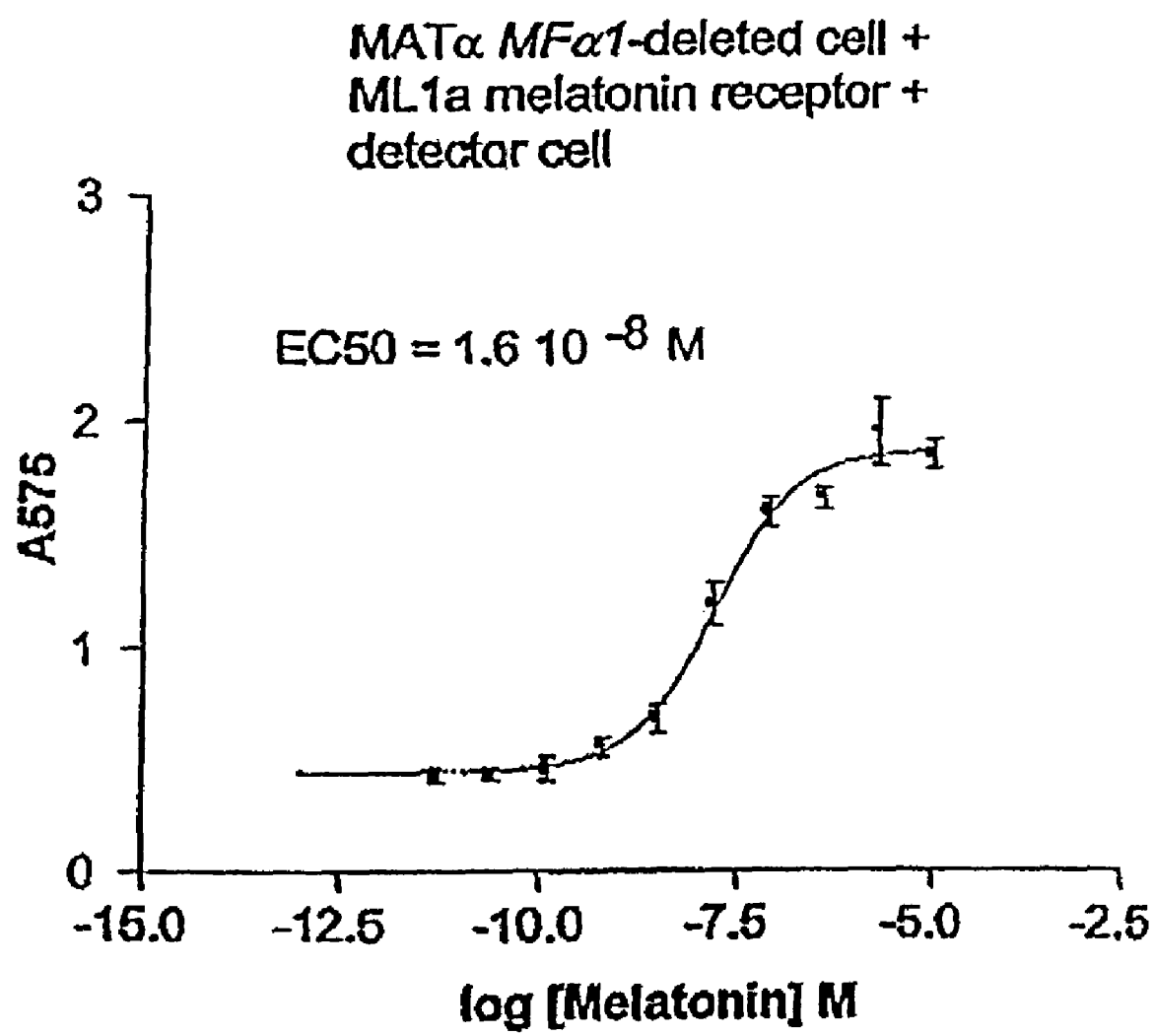
FIG. 2 shows the dose-response curve for induction of α-factor production in ML1a receptor-expressing MATα test cells deleted for the MFα1 gene, as detected by MATa detector cells upon stimulation with various concentrations of melatonin.

As shown in FIG. 2, the activity of β-galactosidase in the detector cells was dependent on the concentration of melatonin to which the test cells were exposed. This dose-dependence indicates that not only are the test cells able to secrete different amounts of α-factor in accordance with the degree to which the receptor of interest is activated, but also that the β-galactosidase activity in the detector cells mirrors the changes in ligand concentration over a pharmaceutically useful range. Furthermore, the assay displays great sensitivity, yielding an EC50 for melatonin in the range of 0.5 to 16 nanomolar.

This method for using ligand-induced mating factor production in MFα1-deleted cells as an indicator of the activity of the mating factor response pathway has been shown to work with several different mammalian receptors. Detection of LacZ activity in the detector cells (data shown in Table 6) was performed essentially as described in the experimental protocol of Example 1, with the exception that 20 microliters of a solution containing 0.5 mM fluorescein di-β-D-galactopyranoside (FDG), 125 mM PIPES pH 7.2, 1.25% Triton X-100 was added instead of the 20 microliters of CPRG solution utilized in Example 1. Following addition of the FDG solution, the reaction was incubated for 30 minutes at 37° C. After stopping the reaction with 20 microliters of 1 M $Na_2CO_3$, the fluorescence was determined utilizing a 96-well plate reader with an excitation wavelength of 485 nm and an emission wavelength of 535 nm. FDG was used rather than the CPRG substrate because the fold induction observed with FDG as the fluorescent substrate was several fold higher than that with CPRG (a 20 fold induction versus a 5 fold induction in experiments containing the ML1a receptor). This was likely due to a decreased sensitivity on the part of FDG to cellular background material.

TABLE 6

Fold induction at saturating or near saturating concentrations of ligand for various G-protein coupled receptors expressed in yeast (n.d. = not determined).

| Receptor |  | Strain | Plasmid | Ligand | Test Cell + FUS1p-lacZ plasmid | Test cell + Detector Cell |
|---|---|---|---|---|---|---|
| ML1a | Melatonin 1A Receptor | CY18592 | CP2695 | melatonin | 50 | 20 |
| ML1b | Melatonin 1B Receptor | CY18592 | CP3693 | melatonin | 30 | 20 |
| NPY-Y1 | Neuropeptide Y Y1 Receptor | CY18592 | CP5513 | NPY | 20 | 10 |
| NPY-Y2 | Neuropeptide Y Y2 Receptor | CY18592 | CP5517 | NPY | 4 | 4 |
| NPY-Y5 | Neuropeptide Y Y5/2 Receptor | CY18592 | CP6073 | NPY | 25 | 20 |
| GHSR | Growth Hormone Secretagoge Receptor | CY18879 | CP6416 | GHRP-6 | 9 | 4 |
| A1 | Adenosine 1 Receptor | CY18776 | CP5095 | NECA | 8 | 20 |
| A2a | Adenosine 2A Receptor | CY18782 | CP1766 | NECA | n.d. | 19 |
| A2b | Adenosine 2B Receptor | CY18634 | CP6281 | NECA | n.d. | 26 |
| BK2 | Bradykinin 2 Receptor | CY18778 | CP1930 | Bradykinin | 101 | 84 |
| BRS3 | Bombesin 3 Receptor | CY18908 | CP6161 | Bombesin (6–14) | 15 | 28 |
| CRF1 | Sauvagine Receptor | CY18592 | CP5396 | Sauvagine | 81 | 55 |
| NT1 | Neurotensin 1 Receptor | CY18632 | CP4259 | Neurotensin | 139 | 22 |
| SST2 | Somatostatin 2 Receptor | CY17911 | CP3776 | Somatostatin | 22 | 5 |
| R-VIP-1 | Rat Vasopressin Receptor | CY18636 | CP4110 | Vasopressin | 20 | 8 |
| PAF | Platelet activating factor Receptor | CY18592 | CP1304 | PAF | 44 | 16 |

For certain receptors, such as A1 and BRS3 (Table 6), the fold induction by ligand was approximately twofold higher when determined using the mating factor detection assay than in controls in which the receptors and reporter plasmids were expressed in the same cell type. This indicates that the mating factor detection assay of this invention is in some cases significantly more sensitive than the existing technology.

Incorporation by Reference

All patents, published patent applications and other references disclosed herein are hereby expressly incorporated herein in their entireties by reference.

EQUIVALENTS

Those skilled in the art will recognize, or will be able to ascertain using no more than routine experimentation, many equivalents to the specific embodiments of the invention described herein. Such equivalents are intended to be encompassed by the following claims.

What is claimed is:

1. A method for identifying a compound that modulates a heterologous G protein-coupled receptor in a yeast cell, said method comprising:
   providing a first recombinant yeast cell which comprises a heterologous G protein-coupled receptor that is functionally integrated into a first pheromone response signal transduction pathway of said first yeast cell, wherein a signal molecule is produced by said first yeast cell upon activation of said first signal transduction pathway;
   providing a second recombinant yeast cell that does not comprise a heterologous G protein coupled receptor, but comprises a reporter gene, which produces a detectable signal upon activation of a second signal transduction pathway of said second yeast cell, in response to production of said signal molecule by said first yeast cell;
   contacting said first yeast cell with a test compound;
   contacting said second yeast cell with said signal molecule produced by said first yeast cell; and
   detecting said detectable signal produced by said second yeast cell, thereby identifying a compound that modulates a heterologous G protein-coupled receptor in a yeast cell.

2. The method of claim 1, wherein said second yeast cell further comprises a receptor for said signal molecule, wherein said receptor is functionally integrated into a second pheromone response signal transduction pathway of said second yeast cell such that a activation of said second pheromone response signal transduction pathway causes transcription of said reporter gene, said transcription providing said detectable signal.

3. The method of claim 1, wherein said first and second yeast coils are of opposite mating types.

4. The method of claim 2, wherein said first cell is a MAT S. cerevisiac cell and said second cell is a MATa S. cerevisiae cell.

5. The method of claim 3, wherein said reporter gene is operatively linked to a pheromone responsive promoter.

6. The method of claim 5, wherein said reporter gene is selected from the group consisting of lacZ, HIS3 and LEU2, and said pheromone responsive promoter is FUS 1.

7. The method of claim 4, wherein said MAT S. cerevisiae cell has the endogenous MF1 gene inactivated.

8. The method of claim 7, wherein said MF1 gene is inactivated by deletion.

9. The method of claim 7, wherein said MF1 gene is inactivated by mutation.

10. The method of claim 2, wherein said receptor in said second yeast cell is STE2 or STE3.

11. The method of claim 4, wherein said signal molecule is a protein secreted by said first cell.

12. The method of claim 11, wherein said secreted protein is MF.

13. The method of claim 12, wherein said heterologous G protein-coupled receptor is selected from the group consisting of molatonin receptor 1a, galanin receptor 1, neurotensin receptor, adenosine receptor 2a, somatostatin receptor 2, and corticotropin releasing factor receptor 1a.

14. The method of claim 13, wherein said heterologous G protein-coupled receptor is melatonin receptor 1a.

15. The method of claim 1, wherein said first yeast cell further comprises a heterologous Gα protein.

16. The method of claim 15, wherein said heterologous Gα protein is a chimeric Gα protein.

17. The method claim 15, wherein said heterologous Gα protein is a mutated Gα protein.

18. The method of claim 1, wherein said heterologous G protein-coupled receptor functionally couples to the endogenous yeast GPA-1 protein subunit.

19. The method of claim 1, wherein said test compound comprises a heterologous test polypeptide expressed by said first yeast cell, wherein said heterologous test polypeptide is transported to a location allowing interaction with the extracellular region of said heterologous receptor, and wherein said heterologous test polypeptide is expressed at a sufficient level such that modulation of the signal transduction activity of said heterologous receptor by the heterologous test polypeptide generates said signal molecule.

20. The method of claim 19, wherein said heterologous test polypeptide includes a signal sequence that facilitates transport of the polypeptide to a location allowing interaction with the extracellular region of the receptor.

21. The method of claim 15, wherein said heterologous Gα protein is a mammalian Gα protein.

22. A method for detecting a heterologous gene product produced by a yeast cell comprising:
   causing a first recombinant yeast cell comprising a heterologous G protein coupled receptor to transmit a signal through a pheromone response signal transduction pathway of said first yeast cell, such that a heterologous gene product is produced by said first yeast cell upon transmission of said signal through said signal transduction pathway; and
   contacting said heterologous gene product with a second recombinant yeast cell that does not comprise a heterologous G protein coupled receptor, but comprises a reporter gene, which produces a detectable signal upon activation of a signal transduction pathway of said second yeast cell,
   detecting said detectable signal produced by said second yeast cell, thereby detecting said a heterologous gene product produced by said first yeast cell.

23. A method for identifying a compound that modulates production of a heterologous gene product produced by a yeast cell, said method comprising:
   providing a first recombinant yeast cell, comprising a heterologous G protein coupled receptor that is functionally integrated into a pheromone response signal transduction pathway of said first yeast cell, wherein said first yeast cell produces a heterologous gene product upon activation or said signal transduction pathway;

providing a second recombinant yeast cell that does not comprises a heterologous G protein coupled receptor, but comprises a reporter gene, which produces a detectable signal activation of a signal transduction pathway of said second yeast cell, contacting said first yeast cell with a test compound;

contacting said second yeast cell with said heterologous gene product produced by said first yeast cell; and detecting said detectable signal expressed by said second yeast cell, thereby detecting a compound that modulates production of said heterologous gene product produced by said first yeast cell, contacting said first yeast cell with a test compound;

contacting said second yeast cell with said heterologous gene product produced by said first yeast cell; and detecting said detectable signal expressed by said second yeast cell, thereby detecting a compound that modulates production of heterologous gene product produced by said first yeast cell.

* * * * *

UNITED STATES PATENT AND TRADEMARK OFFICE
CERTIFICATE OF CORRECTION

PATENT NO.         : 7,090,991 B2
APPLICATION NO. : 10/404018
DATED                 : August 15, 2006
INVENTOR(S)        : Lambertus J. Oehlen It is certified that error appears in the above-identified patent and that said Letters Patent is hereby corrected as shown below:

Col. 39, in Claim 3, Line 54, after the word "yeast" please delete "coils" and replace with --cells--.

Col. 40, in Claim 22, Line 48, after the word "pathway:" please delete ":and".

Col. 40, in Claim 22, Line 54, after the word "cell" please add --; and--.

Signed and Sealed this

Twelfth Day of December, 2006

JON W. DUDAS
*Director of the United States Patent and Trademark Office*